(12) United States Patent
Stroup et al.

(10) Patent No.: US 10,549,028 B2
(45) Date of Patent: *Feb. 4, 2020

(54) MEDICAL INFUSION DEVICE AND METHODS OF USE

(71) Applicant: Alliance Vascular Devices LLC, Santee, CA (US)

(72) Inventors: David Stroup, Santee, CA (US); Arthur Deptala, Santee, CA (US); Jonas Cochran, Santee, CA (US)

(73) Assignee: Alliance Vascular Devices, LLC, Santee, CA (US)

(*) Notice: Subject to any disclaimer, the term of this patent is extended or adjusted under 35 U.S.C. 154(b) by 174 days.

This patent is subject to a terminal disclaimer.

(21) Appl. No.: 15/283,968

(22) Filed: Oct. 3, 2016

(65) Prior Publication Data

US 2017/0021090 A1 Jan. 26, 2017

Related U.S. Application Data

(63) Continuation-in-part of application No. 14/704,221, filed on May 5, 2015, now Pat. No. 9,457,144, which (Continued)

(51) Int. Cl.
*A61M 5/142* (2006.01)
*A61M 39/22* (2006.01)
(Continued)

(52) U.S. Cl.
CPC ............ *A61M 5/142* (2013.01); *A61M 5/165* (2013.01); *A61M 5/3257* (2013.01); *A61M 39/22* (2013.01)

(58) Field of Classification Search
CPC .............. A61M 5/1408; A61M 5/1582; A61M 5/3232; A61M 5/326; A61M 5/3271;
(Continued)

(56) References Cited

U.S. PATENT DOCUMENTS 3,354,881 A 11/1967 Bloch
4,632,671 A 12/1986 Dalton
(Continued)

FOREIGN PATENT DOCUMENTS

EP 1048311 A2 11/2000
FR 2941867 8/2010
(Continued)

OTHER PUBLICATIONS

PCT/US2014.056109 International Search Report and Written Opinion dated Dec. 1, 2014.
JP2019-543972 Office Action dated Apr. 23, 2019.

*Primary Examiner* — Nathan R Price
*Assistant Examiner* — Justin L Zamory
(74) *Attorney, Agent, or Firm* — Wagenknecht IP Law Group PC

(57) ABSTRACT

A medical infusion device including a chamber characterized by an upper body joined to a lower body via a reversibly collapsible sidewall. The upper body has a first channel fluidly coupled to a needle and a second channel fluidly coupled to an interior of the chamber. The chamber transitions from a collapsed state to the expanded state to retract the needle by introducing fluid into the interior of the chamber through the second channel.

19 Claims, 28 Drawing Sheets

Related U.S. Application Data is a continuation of application No. 14/541,796, filed on Nov. 14, 2014, now Pat. No. 9,050,130, which is a continuation of application No. 14/488,982, filed on Sep. 17, 2014, now abandoned.

(60) Provisional application No. 61/879,550, filed on Sep. 18, 2013.

(51) Int. Cl.
*A61M 5/165* (2006.01)
*A61M 5/32* (2006.01)

(58) Field of Classification Search
CPC ........ A61M 5/3243; A61M 2005/1585; A61M 2005/325; A61M 2005/14252; A61M 2005/14513; A61M 2005/3226; A61M 2005/1403; A61M 2005/14256; A61M 2005/14284; A61M 2005/3242; A61M 2005/3258; A61M 2005/1581; A61M 2039/1072; F04B 33/00; F04B 45/033; F04B 45/0333
See application file for complete search history.

(56) References Cited

U.S. PATENT DOCUMENTS

| | | |
|---|---|---|
| 5,019,059 A | 5/1991 | Goldberg et al. |
| 5,219,338 A | 6/1993 | Haworth |
| 5,224,936 A | 7/1993 | Gallagher |
| 5,234,411 A | 8/1993 | Vaillancourt |
| 5,487,733 A | 1/1996 | Caizza |
| 5,531,713 A | 7/1996 | Mastronardi et al. |
| 5,885,255 A | 3/1999 | Jaeger, Jr. |
| 6,238,375 B1 | 5/2001 | Powell |
| 6,884,224 B2 | 4/2005 | Dalton |
| 7,238,172 B2 | 7/2007 | Bertheas |
| 7,758,549 B2 | 7/2010 | Barkhahn |
| 8,043,268 B1 | 10/2011 | Marks |
| 8,535,279 B2 | 9/2013 | Schweikert |
| 8,545,455 B2 | 10/2013 | Szucs |
| 8,728,029 B2 | 5/2014 | Vaillancourt |
| 9,050,130 B2 | 6/2015 | Stroup et al. |
| 2003/0168366 A1 | 9/2003 | Hirsiger et al. |
| 2004/0143195 A1 | 7/2004 | Bressler et al. |
| 2004/0158207 A1 | 8/2004 | Hunn et al. |
| 2005/0277882 A1 | 12/2005 | Kriesel |
| 2008/0281297 A1 | 11/2008 | Pesach et al. |
| 2009/0299302 A1 | 12/2009 | Lambert |
| 2009/0306595 A1 | 12/2009 | Shih et al. |
| 2010/0057021 A1 | 3/2010 | Ishikura et al. |
| 2010/0249748 A1 | 9/2010 | Szucs |
| 2011/0028916 A1 | 2/2011 | Schweikert |
| 2011/0028982 A1 | 2/2011 | Lacy |
| 2012/0046621 A1 | 2/2012 | Vaillancourt et al. |
| 2012/0065587 A1 | 3/2012 | Barron et al. |
| 2014/0039416 A1 | 2/2014 | Vaillencourt |
| 2015/0080856 A1 | 3/2015 | Stroup et al. |
| 2015/0231331 A1 | 8/2015 | Stroup et al. |

FOREIGN PATENT DOCUMENTS

| | | |
|---|---|---|
| JP | 2001-259034 A | 9/2001 |
| WO | 2007126085 A1 | 11/2007 |

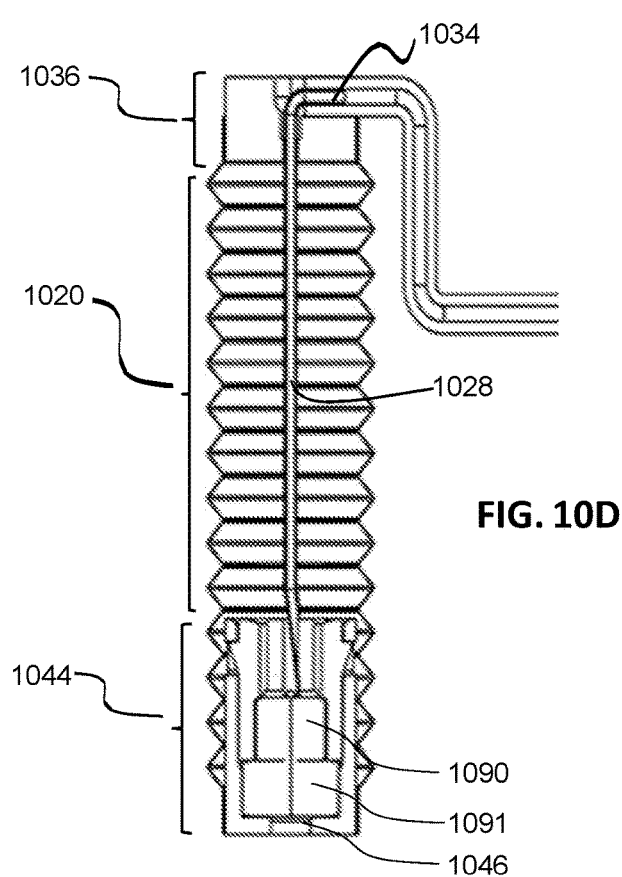
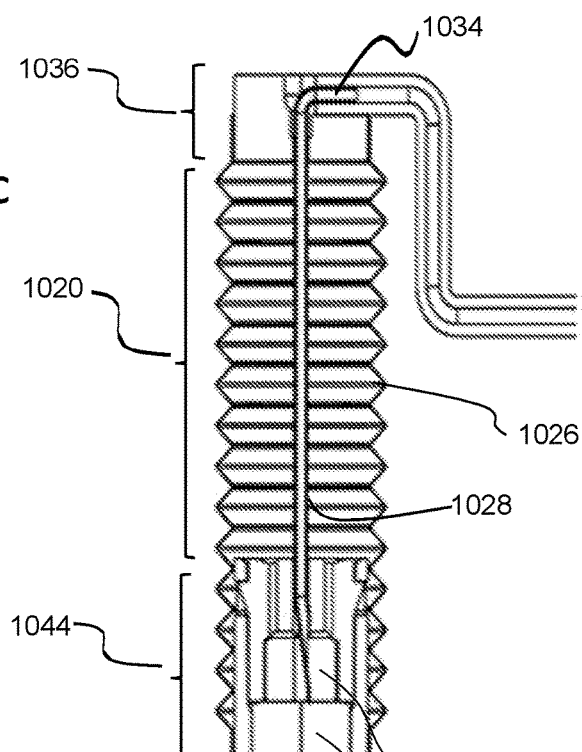
FIG. 10C
FIG. 10D

MEDICAL INFUSION DEVICE AND METHODS OF USE

CROSS REFERENCE TO RELATED APPLICATIONS

This is a continuation in part of U.S. patent application Ser. No. 14/704,221, filed May 5, 2015, which is itself a continuation of U.S. patent application Ser. No. 14/541,796, filed Nov. 14, 2014, now U.S. Pat. No. 9,050,130, which is itself a continuation of U.S. patent application Ser. No. 14/488,982, filed Sep. 17, 2014, now abandoned, which itself claims priority to U.S. provisional patent application No. 61/879,550 filed Sep. 18, 2013. The disclosure of medical infusion devices and methods of use from each is herein incorporated by reference in its entirety.

FIELD OF THE INVENTION

The invention relates generally to medical devices that infuse medical samples into implanted ports connected to the cardiovascular system of patients and more specifically to a medical infusion device having a chamber that volumetrically expands to withdraw and secure a needle after infusion.

BACKGROUND

Infusion devices that incorporate non-coring needles, such as Huber needles, are commonly used in hospitals and medical care facilities to administer chemotherapy, provide intravenous fluids and transfuse blood. Typically these devices are used to administer treatments through a medical port implanted under the skin and connected to a catheter. Accessing the medical port involves inserting the non-coring needle into a septum at the top of the port. The septum is capable of resealing after removal of the non-coring needle, thereby allowing multiple uses of a same port.

While these devices provide a reliable approach to administering treatment to the patient, their use is also associated with considerable risk to the patient and medical professional, most notably the risk of needle stick injuries and the risk of contamination by bloodborne pathogens and exposure to hazardous drugs. Needle stick injuries most commonly occur during the manual removal of the needle from the port. Typically two hands are required to remove the needle, in particular one hand to steady the port in the patient while the other hand forcibly pulls the needle from the port. As the removal of the needle requires some force, at the point the needle becomes free from the skin the sudden release of pressure can cause the needle to rebound—a phenomenon known as 'bounce-back'. During this process the hand the health care professional uses to steady the port is at risk of a needle-stick injury. Needle stick injuries carry with them the risk of contamination by bloodborne pathogens transferred from the patient to the health care professional.

Additionally, such infusion devices are often used to administer toxic substances such as those used for chemotherapy and the like. These substances are designed to kill the cancer cells in the patient however as their effects are not specific to cancerous cells, accidental exposure can put the health care professional at risk. Accidental exposure can occur either as a result of a needle stick injury with a device used to infuse the chemotherapy and/or by leaks or spillage from the needle that can occur after its removal.

Further, such infusion devices often lack pressure bearing structures above their pierceable barriers so as to prevent pressure from their chambers from opening the pierced barrier and leading to an ingress of fluid into a patient's implanted medical port. Such devices also lack a structure that prevents the needle from prying open the pierceable barrier after administration of a drug and causing an ingress of fluid into a patient's implanted medical port.

Therefore there remains a need for a medical infusion device that prevents or reduces needle stick injuries and that prevents or reduces exposure to infusion media by leaks or spillage once the needle is withdrawn from the patient. There also remains a need for a medical infusion device with a pressure bearing structure above its pierceable barrier that also prevents a needle from prying open the pierceable barrier.

SUMMARY

In light of the risks to both health care professionals and the patients associated with the use of medical infusion devices, the present invention provides a medical infusion device in a form that prevents or reduces a likelihood of needle stick injuries, exposure to bloodborne pathogens and exposure to infusion samples.

To this end, in a first aspect of the invention a medical infusion device is provided including a chamber characterized by an upper body joined to a lower body by a reversibly collapsible sidewall. The upper body preferably has two channels. The first channel is fluidly coupled to the lumen of a needle, and the second channel is fluidly coupled to the interior of the chamber at a position distinct and separate from the first channel. Each channel is configured for fluid connection to tubing outside of the chamber. The lower body has a pierceable barrier that can be pierced by the needle.

The chamber has a collapsed state and an expanded state. The collapsed state is characterized as the sidewall being collapsed and the needle piercing entirely through the pierceable barrier. The expanded state is characterized as the needle less than entirely piercing through the pierceable barrier. The chamber is configured to transition from the collapsed state to the expanded state by introducing fluid into the interior of the chamber through the second channel.

The chamber sidewall can be configured to reversibly collapse and expand using a variety of approaches, such as by providing the sidewall in a bellows-like configuration, characterized as having two or more generally linear segments joined by alternating folds at predetermined fold lines. In a further embodiment, the sidewall is formed as two, three, or more segments that concentrically nest in one another in the collapsed state. Alternatively, the chamber sidewall can be formed from a foldable, bendable or crumpling polymer without predetermined fold lines.

During infusion of a sample, such as a medication, the chamber is provided in its collapsed configuration. Volumetric expansion of the chamber retracts the needle at least partially into the chamber. Expansion preferably occurs by introducing a fluid, such as a liquid, into the chamber via the second channel. Volumetric expansion of the chamber lifts the needle through its attachment at the upper body. In some embodiments, the infusion device includes a visual indicator, such as a coloring or colored dye powder or concentrate, housed in the chamber, which when suspended in solution visually indicates the presence of fluid.

In some embodiments, the infusion device includes at least one valve, which may be integrated within the upper body or external and remote from the upper body. In some embodiments the valve only regulates flow of fluid into the first channel and thus through the needle for delivery of an infusion sample into an implanted port of a patient. In other embodiments the valve only regulates flow of fluid into the second channel and thus the chamber interior for volumetric expansion, selectively transitioning the device from the collapsed state to the expanded state. In still other embodiments, the valve selectively directs flow to either the first or second channel and thus between the needle and chamber interior. In still other embodiments, the valve can prevent fluid access to both the first channel and the second channel. In yet another embodiment flow is directed into the chamber and permitted to backwash the needle, the first channel, and connected tubing. In yet another embodiment, the valve is a rotating valve that rotates parallel to the plane of the needle or rotates transfers to the plane of the needle.

In some embodiments, the upper body and lower body are friction fit or have complementary locking structures to lock one another in the collapsed state during infusion and unlock prior to or during volumetric expansion of the chamber after infusion. The complementary locking structures can be twist locks, screw and thread other suitable structures.

The pierceable barrier permits fluid tight withdrawal of the needle into the chamber. Preferably, the pierceable barrier is self-sealing. In some embodiments, the pierable barrier is configured as a lower septum positioned below and preferably adjacent to an upper septum. In further embodiments, the lower septum forms a higher pressure seal compared to the upper septum. In some embodiments the bevel or tip of the needle remains in the upper septum for occlusion and disposal after retraction. In some embodiments, an o-ring encircles the needle for further sealing. In some embodiments the bevel or tip of the needle is fully captured within the chamber such that fluid filling the chamber can backflush the inner lumen of the needle after retraction.

In some embodiments, the chamber deploys a blocking structure to block the needle from piercing entirely through the piercable barrier during or after expansion of the chamber. The blocking structure can be formed as sheet of nonpierceable material, such as metal or metal alloy. The blocking structure can be in the form of a jam lock that wedges against the needle to prevent piercing entirely through the barrier.

In some embodiments, the infusion device includes a mounting base for reversibly mounting the lower body. In such embodiments, the lower body is preferably configured such that the base reversibly accepts the lower body thereby permitting removal of the chamber from the mounting base after expansion of the chamber. That is, the pierceable barrier can form part of the lower body; and the lower body can be quickly and safely removed from the mounting base. The base and lower body can be friction fit into a throughbore or counterbore in the mounting base or may reversibly interlock through appropriate interlocking structures. In other embodiments, the mounting base is integral with the lower body as a single unit that does not release the chamber.

In some embodiments a cap that fits over the upper body. In further embodiments the cap and base can have complementary locking structures for further securing the chamber in its collapsed state during infusion or for insertion of the needle into a medical port.

In some embodiments, the lower body comprises a rigid sheath extending upward into the chamber and configured to guide the needle during expansion and sheathe the needle in the expanded state. In the collapsed state, the sheath is preferably nested within a recess in the upper body of the chamber and may be friction fit. The sheath may include an access port to improve access to the lumen of the needle when the chamber is expanded for backflushing.

In some embodiments an external mechanical guide is positioned outside of the collapsible sidewall, preferably having an end of travel release that upwardly guides the upper body from the base during expansion and releases the chamber with needle after expansion.

In a related aspect, a medical infusion device is provided, which includes a chamber characterized by an upper body fluidly connected to a needle and joined to a lower body by a reversibly collapsible sidewall. The lower body includes a pierceable barrier that can be pierced by the needle and includes a lower septum positioned vertically beneath an upper septum. The lower septum forms a higher pressure seal compared to the upper septum. The chamber has a collapsed state and an expanded state. The collapsed state is characterized as the sidewall being collapsed and the needle piercing entirely through the lower septum to deliver a fluid outside of the device, and the expanded state is characterized as the needle terminating within or vertically above the upper septum.

In another related aspect, a method of delivering medication into an implanted medical port is provided, which includes: providing the infusion device in the collapsed state; piercing the implanted medical port with the needle; infusing medication into the medical port through the needle via the first channel; and introducing fluid into the chamber via the second channel thereby volumetrically expanding the chamber to withdraw the needle from the medical port.

In embodiments where the piercable barrier is configured as a lower septum positioned below an upper septum, the method can also include retracting the needle completely from the lower septum during expansion. In some embodiments, the bevel or tip of the needle is retracted into the upper septum for occlusion. In further embodiments the bevel or tip of the needle is retracted entirely through the upper septum. In further embodiments the method includes continuing to introduce fluid into the chamber to wash the needle. In still further embodiments, the method includes continuing to introduce fluid into the chamber to backflush the first channel via the needle In another related aspect, a method of delivering medication into an implanted medical port is provided using a dual septum configuration, which includes providing the infusion device in the collapsed state; piercing the implanted medical port with the needle; infusing medication into the medical port through the needle via the first channel; and retracting the needle to terminate into or above the upper septum.

BRIEF DESCRIPTION OF THE DRAWINGS

Embodiments of the invention can be better understood with reference to the following drawings, which are part of the specification and represent preferred embodiments. The components in the drawings are not necessarily to scale, emphasis instead being placed upon illustrating the principles of the invention. And, in the drawings, like reference numerals designate corresponding parts throughout the several views.

FIGS. 10A-D depict an infusion device showing an exemplary dual septum configuration.

DETAILED DESCRIPTION

Figure 1A:
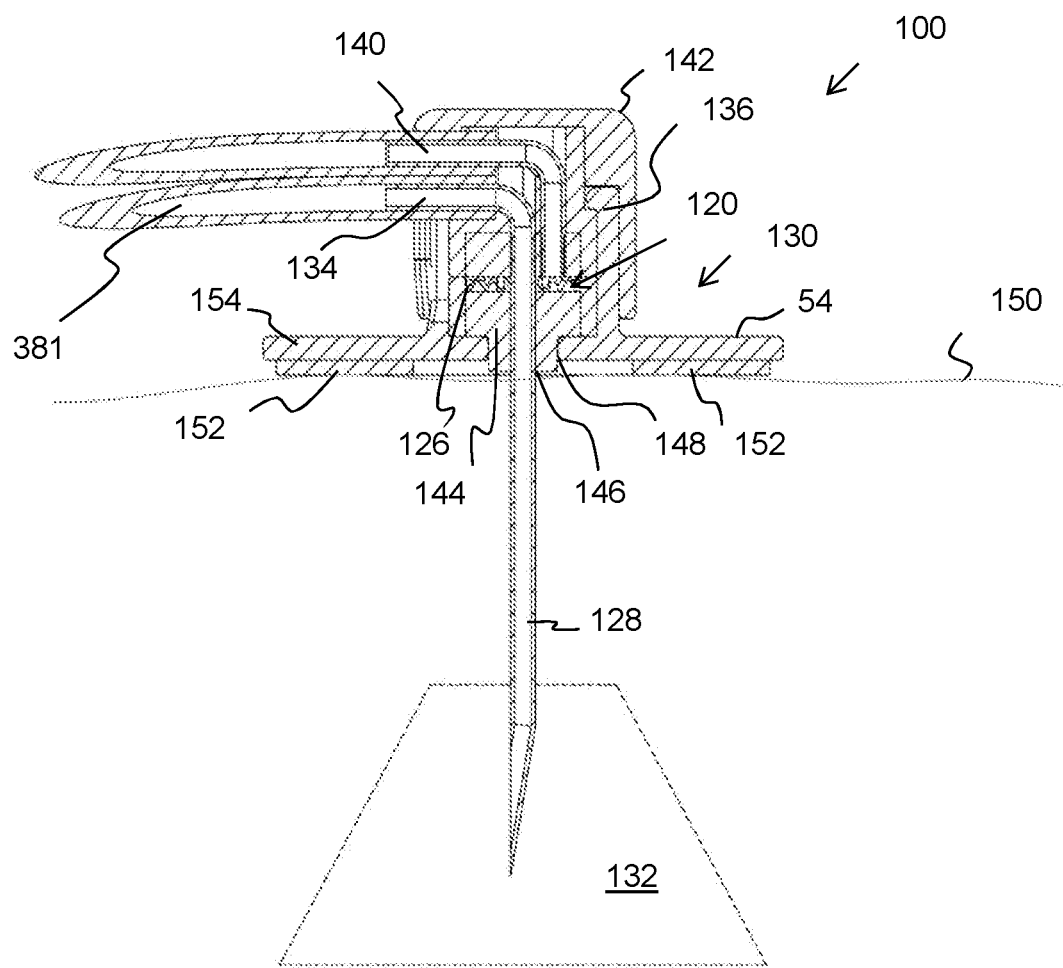
FIGS. 1A-D depict an overview of an exemplary technical approach to medical infusion using a device according to the invention.

The object of the invention is to provide medical infusion devices and related methods that eliminate or reduce the risk of needle stick injuries, contamination by bloodborne pathogens, exposure to hazardous fluids and other risks associated with the use of needles in conventional infusion-based methods. The above is achieved at least in part by providing a medical infusion device that removes an infusion needle from an implanted medical port using a steady or controlled fluidic force, preferably a hydraulic force, thereby reducing bounce-back injury. In addition, the medical infusion device protectively secures a withdrawn needle to avoid further risks of needle stick injury, exposure to contents of the infused sample, and exposure to patient's biological tissue or fluid. Still further, the invention provides a mechanism for backflushing the device to remove residual infusion medication or sample thereby permitting disposal of the device according to non-hazardous standards. Still further, the medical infusion device provides closed systems consistent with medically accepted safety standards. To this end, use of the invention will reduce multiple hazards associated with infusion-based medical treatments and reduce the cost of disposal.

The skilled artisan will appreciate that the infusion devices and accompanying methods can be used in a variety of medical treatments where infusion of a fluid is needed. Among these include medical treatment where the infusion sample is a hazardous fluid or biohazardous fluid, such as a toxin, suspected toxin, whole blood or components of whole blood. Hematology and oncology patients frequently require regular infusions and therefore are nonlimiting intended patients for the device and methods. The skilled artisan will also appreciate that the medical infusion devices and methods may be connected to a variety of pumps, gravity-based drip systems, syringes and other devices that can apply a compressed or hydraulic force to administer fluids to the infusion device.

For clarity of disclosure, and not by way of limitation, the invention is discussed according to different detailed embodiments; however, the skilled artisan would recognize that features of one embodiment can be combined with other embodiments and is therefore within the intended scope of the invention.

Unless defined otherwise, all technical and scientific terms used herein have the same meaning as is commonly understood by one of ordinary skill in the art to which this invention belongs. If a definition set forth in this document is contrary to or otherwise inconsistent with a well-accepted definition set forth in the art, the definition set forth in this document prevails over a contradictory definition.

The term "medical port" or "implanted port" as used herein refers to medical device that is installed beneath the skin of a patient and connected to a catheter, which fluidly connects the port to the circulatory system of the patient, typically a vein. A medical port is conventionally accessed by piercing a septum with a non-coring needle, typically referred to as a Huber needle, to access the port's interior chamber, which is coupled to a catheter for delivery into the patient's circulatory system.

The term "infusion" as used herein refers to the transfer of a fluid, such as medication or nutrients, into a patient's circulatory system. The term "infusion" is also intended to include "transfusions", such as transfusion of whole blood or components of whole blood, including but not limited to red blood cells, while blood cells, plasma, clotting factors, and platelets.

The term "fluid" as used herein refers to a substance that continually deforms under an applied shear stress. A "fluid" can be liquid or gas but is preferably liquid. Medications are typically in liquid form when infused into the patient's circulatory system through the device. Volumetric expansion of the chamber can use gas as the fluid but preferably uses liquid.

The term "fluidly coupled" or "fluidly connected" as used herein refers to the joining of two structures, each having a lumen through which a fluid may pass. A variety of complementary structures are known in the art for fluid coupling. Among these include luer locks, syringe adapters, and complementary mating structures having a central lumen.

The term "two channels that do not intersect in the upper body" as used herein refers to two channels that are spatially separated from one another such that a fluid cannot pass continuously from one channel to the other without passing through the chamber.

The term "position distinct and separate" as used herein refers to two independent positions that are not shared. The first and second channels exit the upper body at distinct and separate positions and thus do not share an exit aperture.

The term "pierceable barrier" as used herein refers to a surface that may be pierced by a needle and is preferably a self-sealing septum.

The term "self-sealing" as used herein refers to the ability of the barrier to form a fluid or liquid tight seal upon withdrawal of a needle. Self-sealing materials are commonly used in the construction of septums for repeated piercing by needles and are incorporated herein by reference.

The term "blocking structure" as used herein refers to a structure that prevents a needle from entirely traversing the pierceable barrier. The "blocking structure" can be a "nonpierceable blocking structure", which as used herein refers to a structure positioned between the tip of the needle and the pierceable barrier, the structure formed from a material, such as metal or metal alloy, which cannot be pierced by a needle having a gauge consistent with infusion of medication into a human. Other suitable blocking structures include a jam lock that wedges against the needle when the chamber is in an expanded state to prevent passage of the needle entirely through the barrier.

The term "closed system" as used herein refers to a medical device that mechanically prohibits the transfer of environmental contaminants into the system and escape of hazardous drug or vapor concentrations outside the system. A "closed system" is leakproof and airtight.

The term "collapse in a concentrically nested manner" as used herein refers to two or more segments able to fit within one another in the collapsed state such that they are in substantial vertical alignment with one another.

Reference will now be made in detail to non-limiting embodiments of the present invention by way of reference to the accompanying drawings, wherein like reference numerals refer to like parts, components, and structures.

Figure 1B:
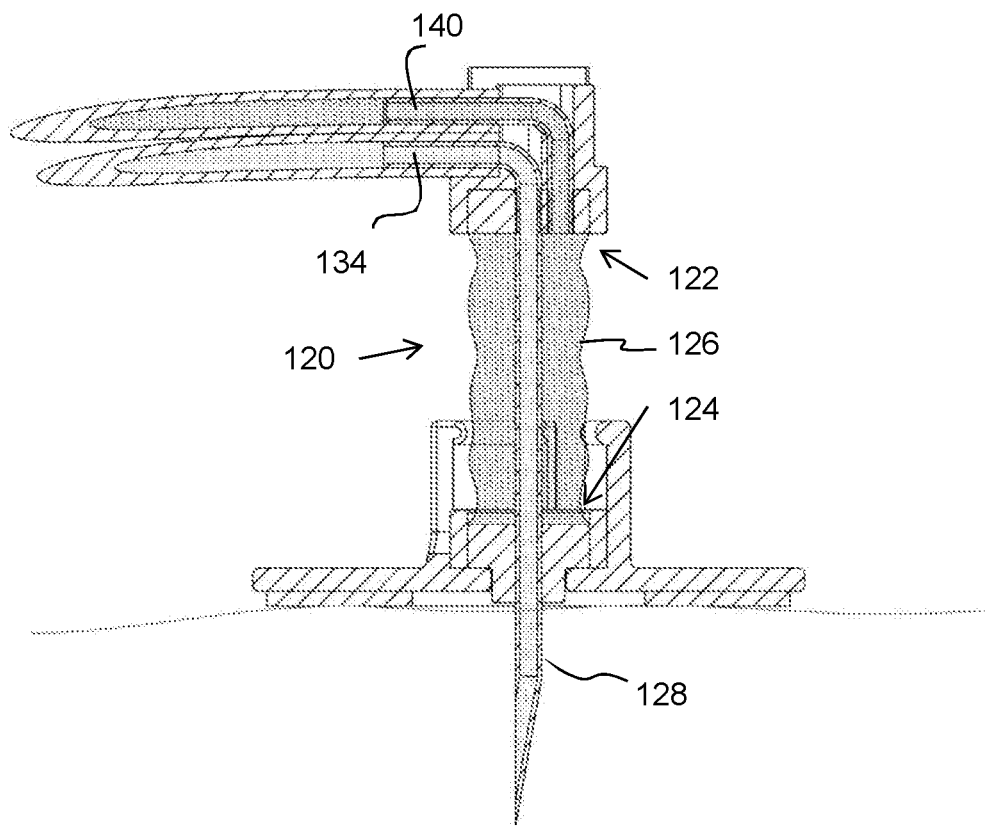
Figure 1B:
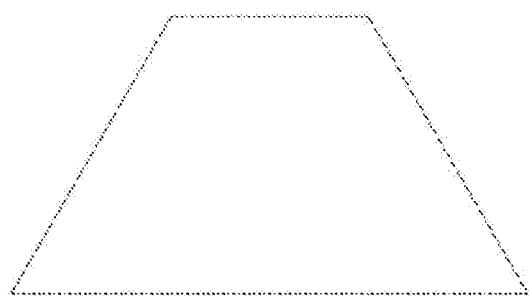
Figure 1C:
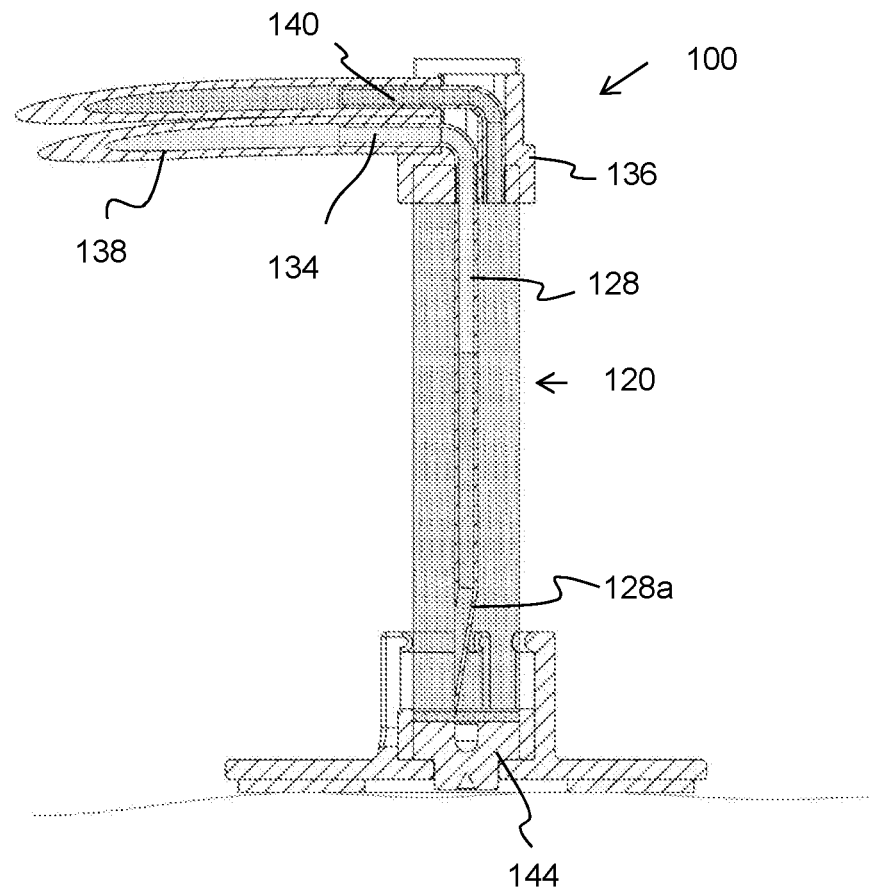
Figure 1C:
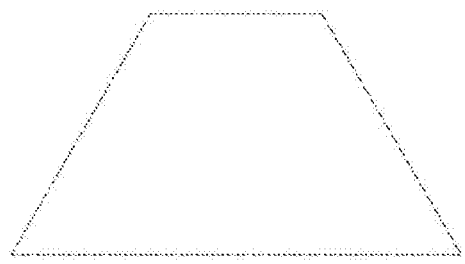

Turning to the drawings, FIGS. 1A-D provide an overview of a preferred technical approach used by the invention to infuse medication into a patient and to reduce risk of injury and adverse exposure by both patient and medical professional while conducting the medical procedure. Collectively, FIGS. 1A-D depict a medical infusion device 100, which includes a chamber 120 having an upper end 122, a lower end 124 and a sidewall 126, characterized in that the chamber 120 has a collapsed state (FIG. 1A) and an expanded state (FIG. 1C). As shown in FIG. 1A, the collapsed state is further characterized as having a needle 128, preferably a non-coring or Huber needle, passing through a mounting base 130 and capable of accessing a patient's implanted medical port 132. When in the collapsed state, fluid connection between a remote pumping source, such as a syringe or infusion pump, and the needle 128 is accomplished in part through a first channel 134 within an upper body 136, which itself is positioned at the upper end 122 of the chamber 120. In particular, the first channel 134 of the upper body 136 acts as a conduit to fluidly connect the needle 128 to tubing 138, which itself connects to the remote pumping source, such as the syringe or infusion pump for supplying the infusion medication or infusion sample. The needle 128 is affixed to an upper body 136 at the upper end 122, such that upward movement of the upper body 136 upwardly moves the needle 128. A fluid, such as a liquid medication, can pass through the first channel 134, through the needle 128 and into the patient's implanted medical port, and thus circulatory system. In contrast, FIG. 1C depicts a volumetrically expanded state, characterized as having the chamber 120 fluidly coupled to the needle 128. That is, fluid (liquid or gas) retained within the chamber 120 during expansion can access the lumen of the needle 128 through the bevel/aperture 128a. In this state, the bevel 128a of the needle 128 can be housed within the chamber 120 thereby preventing or reducing exposure between the needle 128 and the patient or medical professional after the infusion procedure. Also in this state, the needle 128, first channel 134, and tubing 138 are ready for washing. Washing is accomplished by backflushing the needle 128, first channel 134 and connected tubing 138 by continuing to add fluid to the expanded chamber, thereby removing residual infusion medication or sample from the device 100, which decreases the cost of disposal since the contents are no longer hazardous. For completeness, FIG. 1B depicts the device 100 transitioning from the collapsed state of FIG. 1A to the volumetrically expanded state of FIG. 1C by filling the chamber 120 with a fluid through a second channel 140 within the upper body 136.

Turning back to FIG. 1A, the infusion device 100, like the other embodiments herein, can be initially provided in the expanded state, but it is preferably initially provided in the collapsed state. If provided in the expanded state a through passage having a hydrophobic filter, preferably at the upper body 136, can be provided to permit outgassing of the chamber 120 while collapsing the chamber 120. The devices 100 can be supplied using sterile packaging methods known in the infusion arts, such as providing a plurality of sterile, individual devices 100 with the needles 128 covered by protective covers and sealed in tear-away or peel-away packaging to ensure sterility and safety. Tubing 38, such as polymer medical tubing connected at its proximal end to an infusion pump or syringe, can be fluidly coupled at its distal end to the first channel 134 or second channel 140 through any suitable connecting structure that permits passage of a fluid, such as couplings, conduits, adapters, connectors, barbed connectors, luer locks or other suitable connecting structures. Connection can be accomplished using snap fit connection, friction fit connection, male to female connection, tongue and groove connection or other approaches known in the medical device arts for fluidly connecting structures for the passage of fluid, and in particular liquid medication.

Also shown in FIG. 1A, the collapsed state is further characterized as having the upper body 136 in close proximity to a base 130 due to the minimal volume within the chamber 120, which can be accomplished by providing a chamber sidewall 126 that is folded, bent, crumpled or collapsed. In some embodiments, the chamber 120 can include a sidewall 126 that is formed from a bendable material that permits the bending or folding of the sidewall 126 at varying regions along its height without following a predetermined path or fold line thereby permitting the volume within the chamber 120 to be reduced by bending, folding or crumpling the sidewall 126. In other embodiments, the chamber 120 includes a bellows configuration or a more ordered folding by following predetermined fold lines. In related embodiments the chamber 120 is formed in part from segments that concentrically nest in the collapsed state.

Turning to FIG. 1B, expanding the chamber 120 involves introducing fluid into the chamber 120 thereby upwardly extending the sidewall 126 and pulling the needle 128 from the medical port 132 and into the chamber 120 for protection against needle stick injury, exposure to bloodborne pathogens, an infusion sample, or other hazardous fluids. The chamber 120 can be further guided upward through the addition of an external mechanical guide positioned outside of the collapsible sidewall 126, preferably having an end of travel release, that upwardly guides the upper body 136 from the base 130 during expansion thereby further reducing wobble of the upper body 136 and thus needle 128 during expansion of the chamber 120. The external mechanical guide can be joined at the lower end to the base 130 and at the upper end to the upper body 136 or the cap 142. Upon expansion of the chamber 120 the mechanical guide preferably releases the upper body 136 from the base 130 permitting removal of the chamber 120. Introduction can be by any suitable liquid pump or can be by pressurizing or releasing compressed gas, such compressed air. Preferably, while the sidewall 126 is capable of upward extension it is preferably inelastic and preferably does not stretch. This more effectively applies hydraulic force to remove the needle 128 from the medical port 132 during volumetric expansion of the chamber 120. As such, when configured as a cylinder preferably the sidewall 126 does not significantly bulge radially outward when fully extended. Examples of such materials are well known in the polymer arts such as various polypropylenes, polyethylenes or other flexible polymers. While the sidewall 126 is preferably inelastic, it could be elastic as long as the modulus of elasticity results in upward extension of the upper body 134 in the expanded or deployed state.

Returning to FIG. 1A, preferably the chamber 120 remains in its collapsed state before and during infusion of medication, such as infusion of a pharmaceutical. To this end, a variety of structures have been developed to ensure the chamber 120 remains in its collapsed state as added assurance. In some configurations the sidewall 126 is covered for further protection. In one approach, a removable cap 142 is mounted over the upper body 136 and attached to an outer surface of the base 130, such as by complementary threads in a screw cap, tongue and groove, twist lock configuration, or friction fit. Naturally, the cap 142 can be knurled or textured to facilitate its release or removal from the base 130, such as after infusing medication but before introducing fluid into the chamber 120 for expansion. In other embodiments, the cap 142 can unlock from the base 130 by remain locked to the upper body 136 for pulling the upper body 136.

In another embodiment, the chamber 120 is encouraged to remain in its collapsed state by adding a memory metal or a spiral-like wire structure to the chamber sidewall 126, such as outside of or embedded within the sidewall 126, which requires additional force to upwardly expand the chamber 120. In still other embodiments, magnetic attraction between magnets of opposing poles can ensure the chamber 120 maintains its collapsed state and depolarization of one or more magnets, such as through modulation of an electric current, facilitates its magnetic release.

In embodiments that include a mounting base 130, such as the embodiment depicted in FIGS. 1A-D, the infusion device 100 includes a lower body 144 at the lower end 124 of the sidewall 126 of the chamber 120. In such configurations, the lower body 144 includes a pierceable barrier 146 that retains a fluid tight seal whether or not the barrier 146 is pierced by the needle 128. Preferably the needle is a non-coring needle 128. Such materials are well known in the art including various rubbers, polymers or silicone used as self-sealing septums in the manufacturing of vascular access medical ports 132. In addition, the lower body 144 can be configured to reversibly engage the base 130, such as by twist lock, tongue and groove, snap lock or the other suitable engagement approaches; however, friction fit is most preferred. For instance, the lower body 144 can be friction fit along a circumference or perimeter of a throughbore 148 or a counterbore in the base 130. Therefore, the throughbore 148 or counterbore can permit both snug engagement of the base 130 with the lower body 144 and provide a passage through which a needle 128 may traverse the base 130 when the lower body 144 and base 130 are engaged and the chamber 120 is in its collapsed state.

The device 100 itself can be formed from materials and manufacturing methods well known to those in the medical device field. For instance, the upper body 136, lower body 144, and base 130 may be formed using conventional injection molding techniques with suitable polymers used in the formation of many medical devices, such as polypropylenes. Similarly, the sidewall 126 of the chamber 120 may be formed from a rubber or bendable polymer then melted, adhered or fused to the upper 136 and lower 144 bodies. The pierceable barrier 146 may be formed from resealable silicone rubber, optionally two silicon units of different pressure joined to one another. The lower body 144 may be provided with an aperture that is covered or filled with polymer or silicone to form the pierceable barrier 146. Alternatively, the lower body 144 may itself be formed, at least in part, from a pierceable material, such as one or more self-sealing polymers or silicone to form the pierceable barrier 146.

In view of the above and referring collectively to FIGS. 1A-D, a method of delivering medication into or through an implanted medical port 132 is also provided, which includes providing the infusion device 100 in a collapsed configuration, aligning the needle 128 with an implanted infusion port 132, and pressing the infusion device 100 such that needle 128 pierces the patient's skin 150 (shown generally in FIG. 1A), then into the septum of the implanted port 132. To further assist with insertion or handling, the uppermost portion of the upper body 136, or an uppermost portion of a cap 142, or a portion of the base 130 may be flattened, convex, concave, flanged, or suitably shaped to accept a hand or finger to assist in securely gripping or pressing the infusion device. Once the needle pierces the skin 150 and is inserted into the patient's infusion port 132, the base 130 can be adhesively mounted to the patient through the use of adhesive mounts 152 positioned along the underside of the base 130 or by applying tape over outward extending flanges 154 of the base 130. Infusion of a medical sample is accomplished by delivering the sample into the first channel 134, which is fluidly coupled to the needle 128, and thus the interior cavity of implanted infusion port 132.

After infusion is complete, the device 100 can be prepared for transitioning from a collapsed state to an expanded state thereby removing the needle 128 from the medical port 132 and safely securing the needle 128. The skilled artisan will appreciate that steps in preparing to remove the needle 128 may be performed consistent with the particular approach used for further retaining the infusion device 100 in its collapsed configuration. For instance, in some embodiments a cap 142 is removed to release the upper body 136 from the base 130. However, in some embodiments, such as those where the cap 142 is friction fit, the cap 142 can be removed from the base 130 by delivering sufficient fluid volume into the chamber 120 to overcome the friction fit attachment.

Exemplary removal of the needle 128 from the medical port 132 and/or patient is demonstrated operationally in FIG. 1B, which involves introducing a fluid to volumetrically expand chamber 120 via the second channel 140 to initiate chamber 120 filling and thus upward extension of the chamber sidewall 126. The skilled artisan will appreciate that the fluid may be any suitable fluid such as water, saline, phosphate buffered saline, wash solution, bleach solution or other liquids. Alternatively, compressed gas, such as compressed air, can be applied to the chamber 120. Preferably, fluid is continually introduced at least until the needle 128 is withdrawn from the patient, and preferably until the bevel or tip is completely housed within the chamber 120 thereby surrounding and capturing the needle 128 to avoid injury. Although the sidewall 126 is preferably extendable, it is also preferably inelastic or substantially inelastic such that the sidewall 126 or chamber 120 does not elastically stretch more than 10 percent under filling pressure such that the upper body 134 can pull the needle 128 upwards. The sidewall 126 when expanded is preferably cylindrical as shown in FIG. 1C but could be arc-shaped, partially spherical or any other suitable shape.

In a preferred embodiment, fluid is continually introduced into the chamber 120 after the needle 128 is completely housed within the chamber 120 such that the introduced fluid is volumetrically displaced to backwash the lumen of the 128a of needle 128. The skilled artisan will appreciate that still further introduction of fluid into the chamber 120 via the second channel 140 will continue to push or backwash the lumen 128a of the needle 128, the first channel 134 and any connected tubing 138 or connectors unless obstructed. In some embodiments, a visual indicator is stored in the chamber 120, such as a colored dye or visually detectable compound, which can be provided as a powder or concentrate and that colors the backflushing solution to visually monitor progress of backflushing. In some embodiments a portion of the chamber 120 interior is spray coated with a dye that can be dissolved in the backflushing solution for coloring. By visually monitoring backflushing, the user is notified when any potentially hazardous medication or sample is removed from the device 100 for disposal. Once backflusing is complete any tubes connected to the device can be clamped or removed. Thus, continuing to backwash the first channel 134 and tubing 138 may provide a further safety feature by preventing exposure during detachment of the device 100 from an infusion pump or syringe and allows disposal without classification as a chemical or biohazard.

Figure 1D:
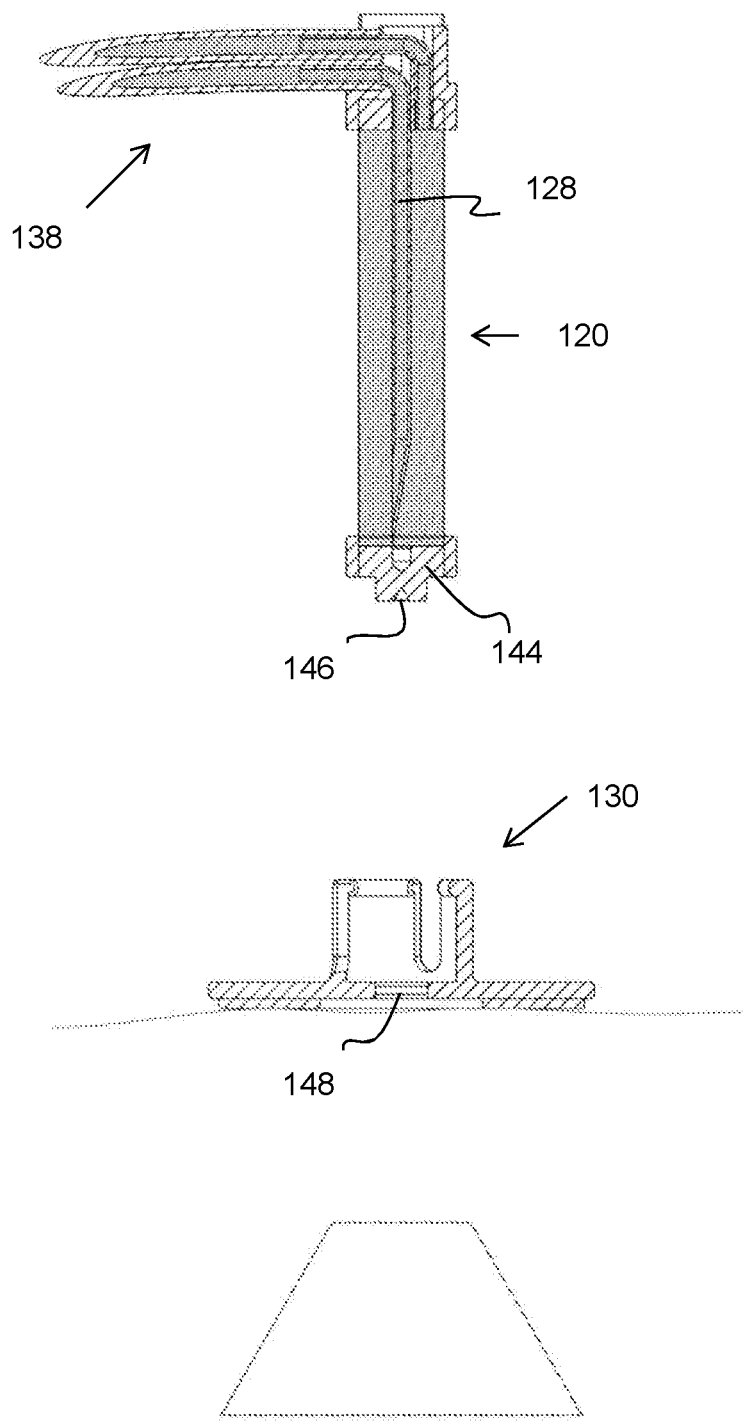

As show in FIG. 1D, the lower body 144 can be disengaged from the base 130 after filling the chamber 120 and capturing the needle 128 without risk of needle stick, exposure to the infused medication or the fluid within the chamber as the pierceable barrier 146 of the lower body 144 maintains a fluid tight seal. That is, the pierceable barrier sufficiently seals the chamber 120 to prevent leaking thereby providing a closed system once the tubes 138 are clamped, a valve integrated into the upper body 142 is closed, or a remote valve positioned away from the upper body 136 is closed. As further protection the chamber 120 may also include a blocking structure configured to block access through the piercable barrier 146 by the needle 128. The base 130 can then be removed from the patient and the infusion device 100 safely disposed.

Figure 2A:
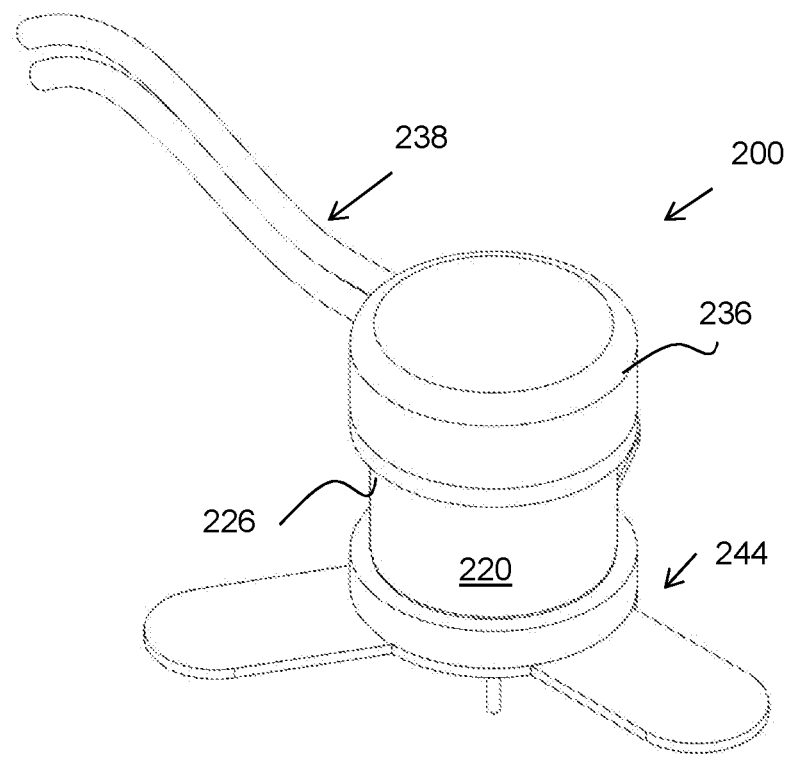
FIGS. 2A-F depict an infusion device showing an exemplary mechanism for a twist lock for use in a collapsed configuration and protectively capturing the tip of the needle within the pierceable barrier when in an expanded state.
Figure 2B:
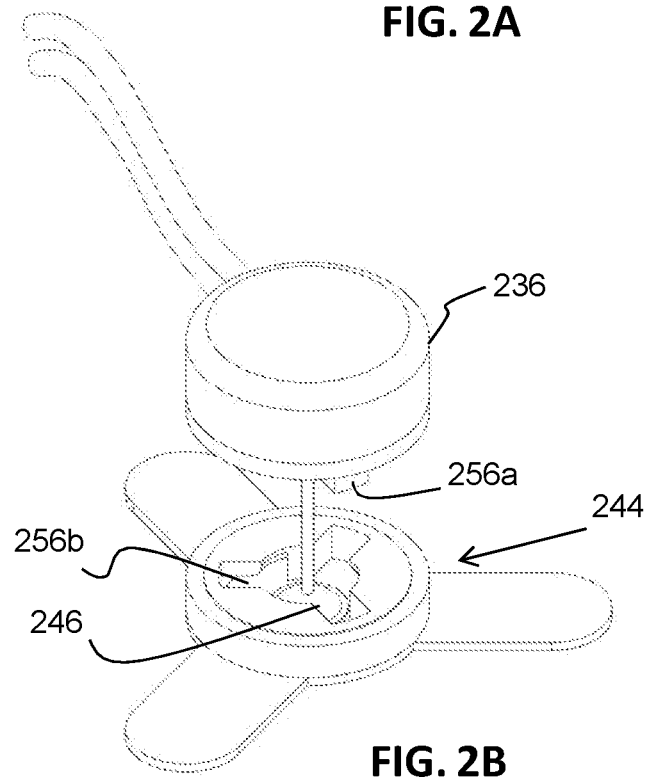
Figure 2C:
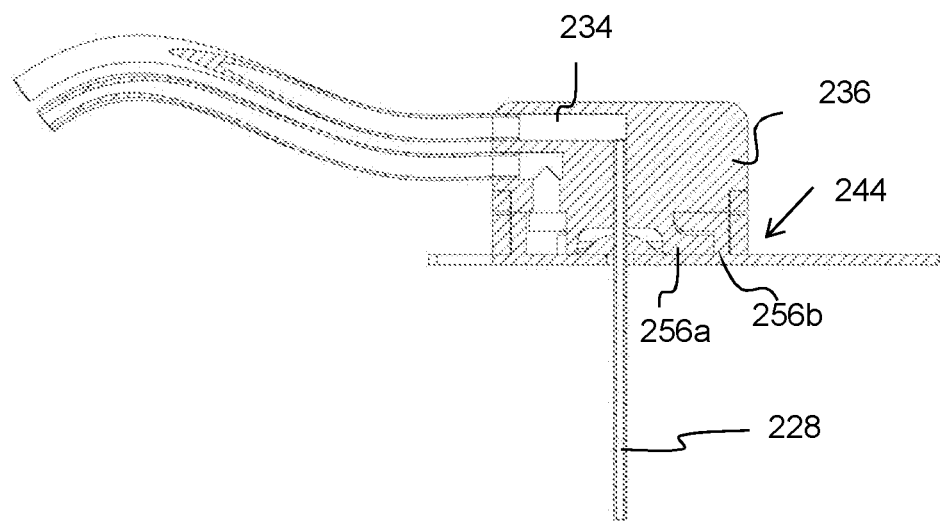
Figure 2D:
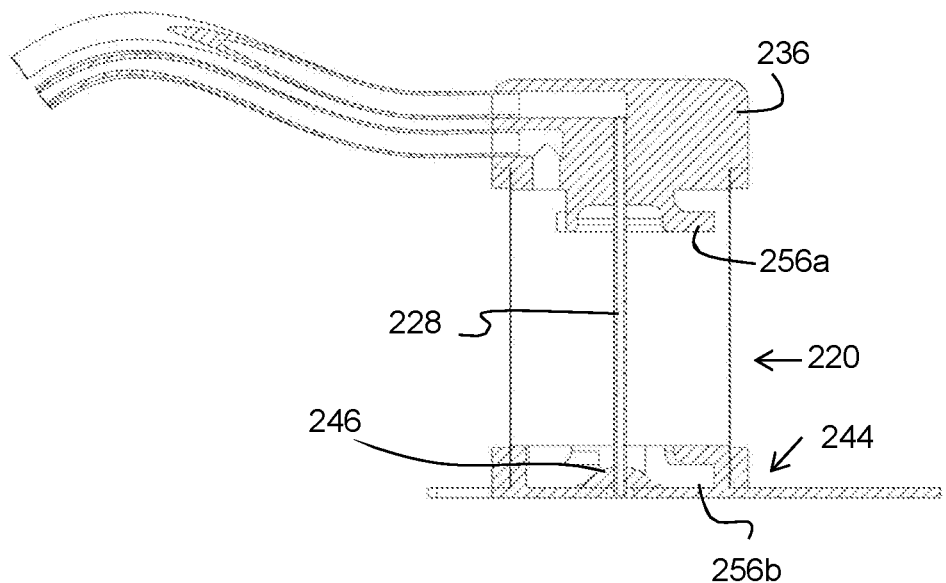
Figure 2E:
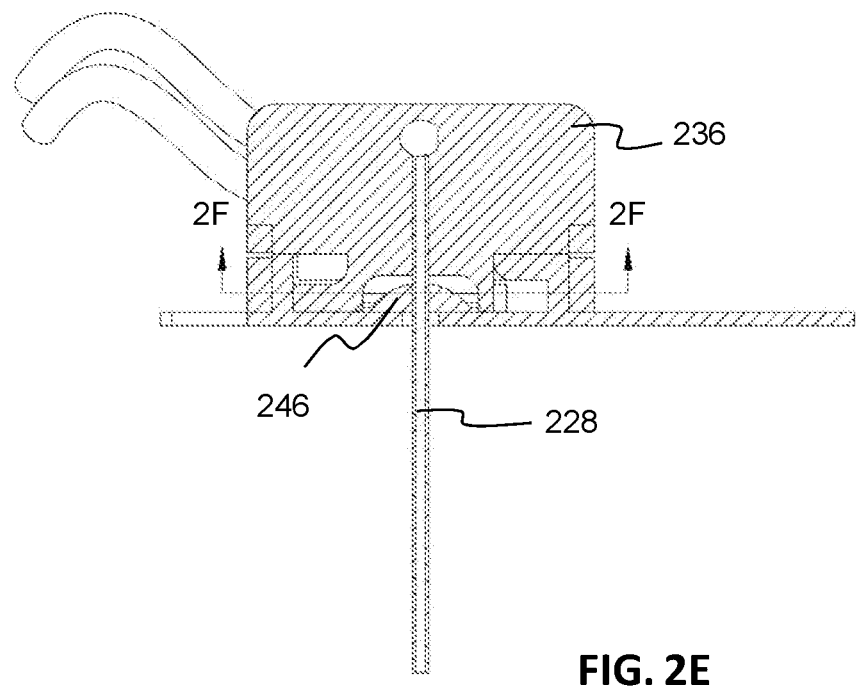
Figure 2F:
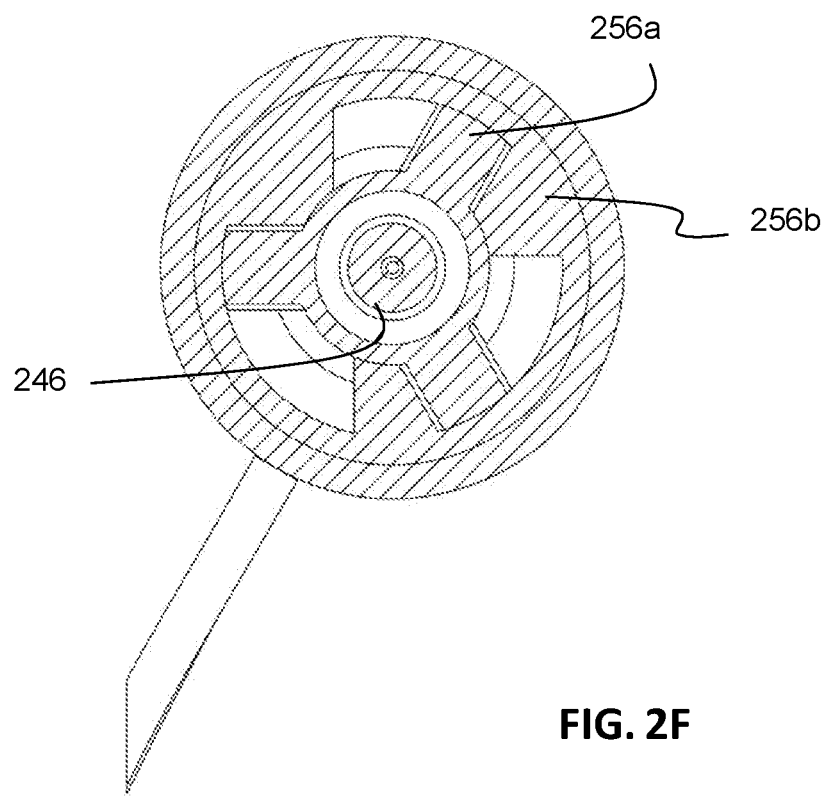

In a related embodiment shown in FIGS. 2A-F, a medical infusion device 200 is provided, which includes a chamber 220 defined by an upper body 236, a sidewall 226, and a lower body 244, characterized in that the chamber 220 has a collapsed state (FIGS. 2C and 2E shown without sidewall 226 for simplification) and an expanded state (FIG. 2D). The skilled artisan would appreciate that the lower body 244 could be divided into a mounting base with lower body insert more akin to FIG. 1 if desired. As shown in FIG. 2C, the collapsed state is further characterized as having a needle 228, preferably a non-coring or Huber needle affixed to the upper body 236, passing through the pierceable barrier 246 of the lower body 244 and thus being capable of accessing a patient's implanted medical port. Fluid connection between a remote source, including but not limited to a syringe, infusion pump, and a drip bag, and the needle 228 is accomplished in part through a first channel 234 within an upper body 236, which itself is positioned at the upper end of the chamber 220 (FIG. 2A). In particular, the first channel 234 of the upper body 236 is fluidly connected to the needle 228 and can be fluidly coupled to tubing 238, which itself connects to a remote pumping source such as the syringe or infusion pump. Accordingly, a liquid medication can pass through the first channel 234, through the needle 228 and into the patient.

In contrast, FIG. 2D depicts a volumetrically expanded state (also referred to as a deployed state), characterized as having the bevel of the needle 228 at or above the bottom most plane of the lower body 244 and fluid retained in the chamber 220. For completeness, FIG. 2A depicts the medical device 200 transitioning from the collapsed state of FIG. 2C to the expanded state of FIG. 2D by filling the chamber 220 with a fluid through a second channel 240 within the upper body 236. The chamber 220 can be further guided upward through the addition of an external mechanical guide positioned outside of the collapsible sidewall 226, that upwardly guides the upper body 236 from the lower body 244 during expansion thereby further reducing wobble of the upper body 236 and thus needle 228 during expansion of the chamber 220. The external mechanical guide can be joined at the lower end to the lower body 244 and at the upper end to the upper body 236.

It is notable that the two channels, 234, 240, do not intersect in the upper body 236. That is, the first channel 234 and the second channel 240 do not directly, fluidly communicate with one another within the upper body 236. In the collapsed state (FIG. 2C), the first channel 234 is connected to the needle 228 to infuse medication directly into the patient. In the expanded state (FIG. 2D), preventing the intersection between the first channel 234 and second channel 240 within the upper body 236 effectively cleans the outside and inside surfaces of the needle 228 from hazardous blood borne pathogens and toxic medications to protect the user. In particular, by avoiding intersection between the two channels 234, 240 in the upper body 236, wash solution pumped into the second channel 240 passes around and through the needle 228 before passing through the first channel 234 to exit the device 200.

The device 200 can be formed from materials and manufacturing methods known to those in the medical device field. For instance, the upper body 236 and lower body 244 may be formed using conventional injection molding techniques with suitable polymers used in the formation of many medical devices such as polypropylene and other polymers used in the construction of medical devices. Similarly, the sidewall 226 of the chamber 220 may be formed from rubber or foldable polymer then adhered or fused to the upper body 236 and lower body 244. The pierceable barrier 246 may be formed from self-sealing silicone rubber. The lower body 244 may be provided with an aperture that is covered or filled with polymer or silicone to form the pierceable barrier 246. Alternatively, the lower body 244 may itself be formed, at least in part, from a pierceable material, such as a self-sealing polymer to form the pierceable barrier 246.

This embodiment exemplifies features that may be incorporated into other embodiments, namely, the upper body 236 and lower body 244 have complementary interlocking structures 256a, 256b, such as a twist-lock or interlocking bayonet and catch, where the upper body 236 and lower body 244 interlock to further ensure that the chamber 220 (the sidewall 226 removed for simplicity of viewing in FIGS. 2B, C, E, F) remains in a collapsed state during infusion. In addition, as depicted in FIGS. 2B-F, the piercable barrier 246 may be configured to protectively hold the needle 228 when in the device is in the expanded state.

Accordingly, use of the device shown in FIGS. 2A-F can provide a method of delivering medication into or through an implanted medical port, which includes providing the infusion device 200 in a collapsed configuration, aligning the needle 228 with an implanted infusion port, and pressing the infusion device 200 such that needle 228 pierces the patient's skin, then into the septum of the implanted port. To further assist with insertion or handling, the uppermost portion of the upper body 236, or a portion of the lower body 244 may be flattened, convex, concave, flanged, curved or suitably shaped to accept a hand or finger to assist in securely gripping or pressing the infusion device 200. Once the needle 228 pierces the skin and is inserted into the patient's infusion port, the lower body 244 can be adhesively mounted to the patient through the use of adhesive mounts positioned along the underside of the lower body 244 or by applying tape over outward extending flanges of the lower body 244. Infusion of a medical sample is accomplished by delivering the sample into the first channel 234, which is fluidly coupled to the needle 228, and thus implanted infusion port.

After infusion is complete, the upper body 236 is rotated in relation to the lower body 244 such that the interlocking structures 256a, 256b are released. The upper body 236 can then be pulled to retract the needle 228, or a fluid is introduced into the expandable chamber 220 via the second channel 240 to initiate volumetric chamber 220 filling and upward extension of the chamber sidewall 226. The skilled artisan will appreciate that the fluid may be any suitable fluid such as water, saline, phosphate buffered saline, wash solution, bleach solution or other liquids. Alternatively, compressed gas, such as compressed air, can be applied to the chamber 220. Preferably, fluid is continually introduced at least until the needle 228 is withdrawn from the port, and until the bevel or tip of the needle 228 is at or above the lowermost plane of the lower body 244. In the expanded or deployed state the needle 228 may remain captured within the piercable barrier 246, which acts to seal the bottom of the chamber 220 and retain the fluid. The device 200 is then removed from the patient. In other embodiments, the needle 228 is entirely withdrawn into the chamber 220 to permit backflushing of the needle 228, channel 234 and optionally connected tubing 238. As with the embodiment above, a visual indicator may be employed to monitor backflushing to ensure removal of potentially hazardous medication or solution and therefore may notify the user when the device 200 may be disposed of without special designation as a hazardous material. Further protection against needle stick can be accomplished by providing a blocking structure or a nonpierceable blocking structure configured to block access through the pierceable barrier 246 by the needle 228 upon expansion.

Figure 3A:
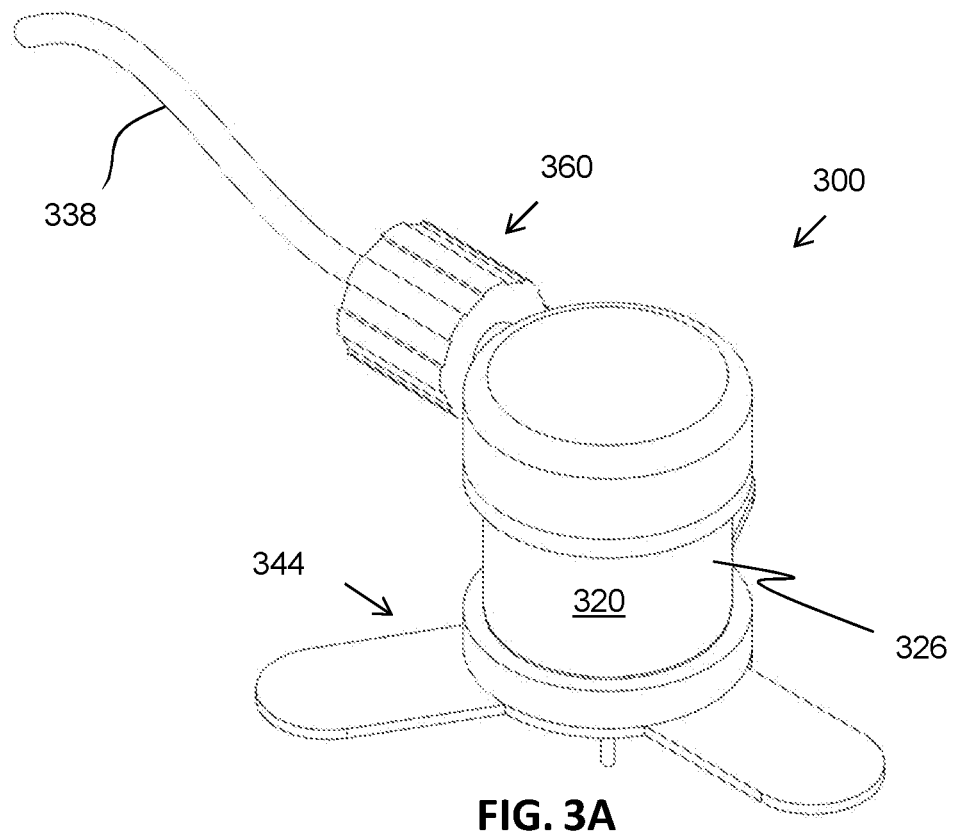
FIGS. 3A-D depict an infusion device showing an exemplary valve mechanism to selectively deliver fluid into different channels of the device from a same exterior tubing.
Figure 3B:
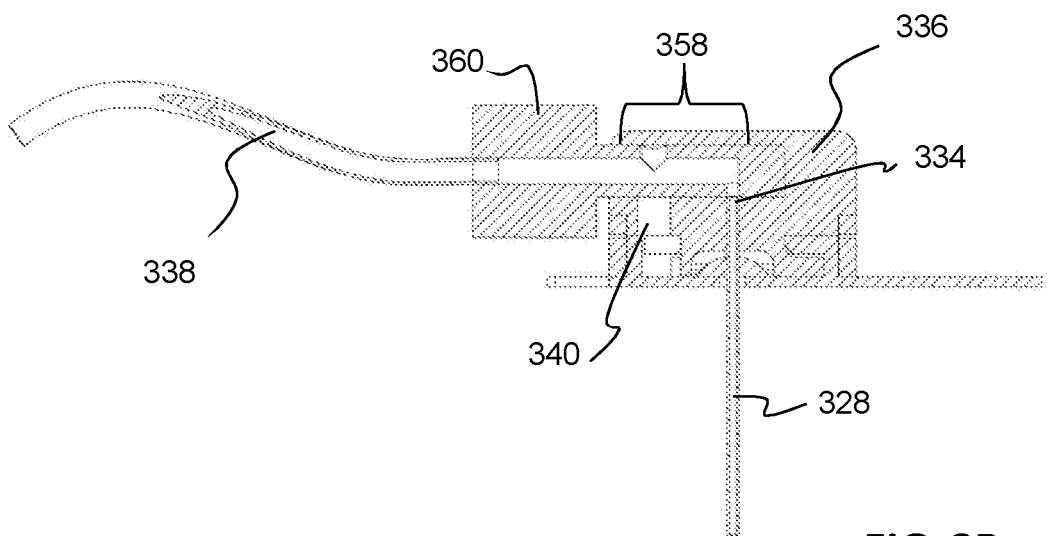
Figure 3C:
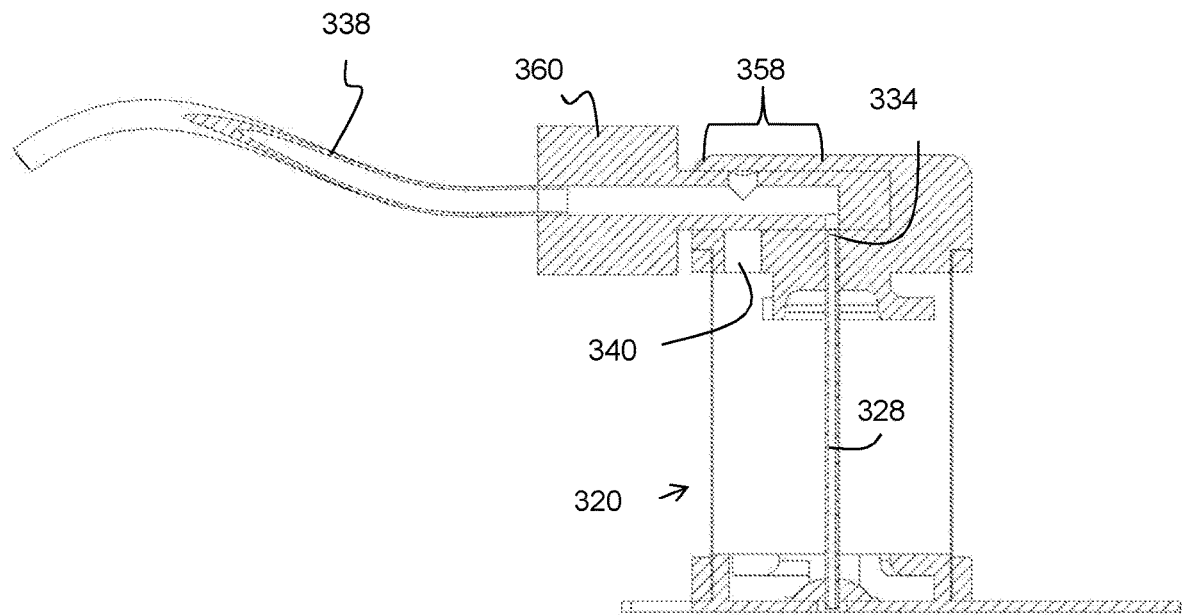
Figure 3D:
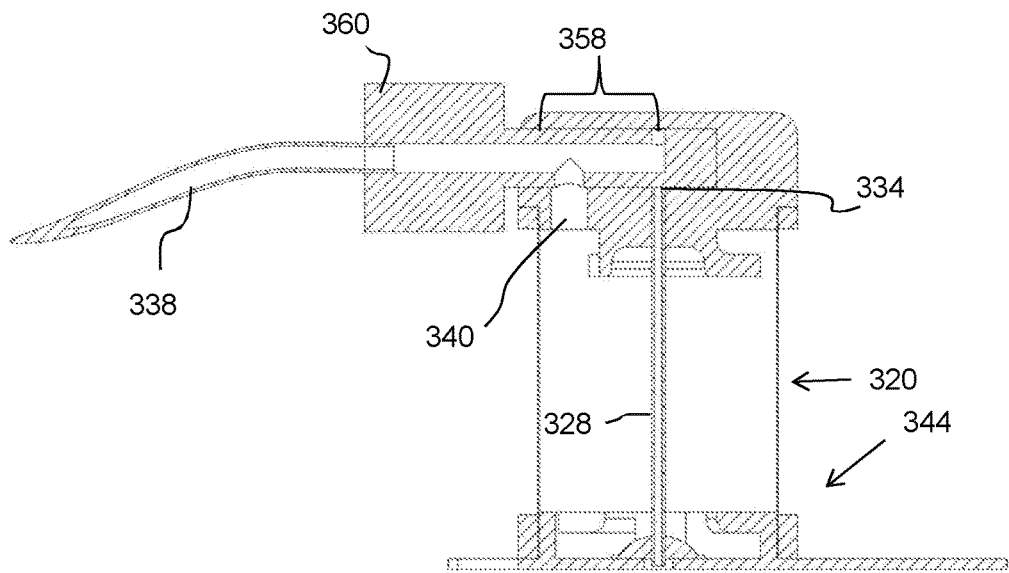

In another related embodiment shown in FIGS. 3A-D, a medical infusion device 300, is provided, which includes a chamber 320 having an upper body 336, a sidewall 326, and a lower body 344, characterized in that the chamber 320 has a collapsed state (FIG. 3B with sidewall 326 removed for simplicity for viewing) and an expanded state (FIG. 3D). The skilled artisan would appreciate that the lower body 344 could be divided into a mounting base with lower body insert more akin to FIG. 1 if desired. As shown in FIG. 3B, the collapsed state is further characterized as having a needle 328, preferably a non-coring or Huber needle affixed to the upper body 336, passing through the lower body 244 and thus being capable of accessing a patient's implanted medical port. Fluid connection between a remote source, including but not limited to a syringe or infusion pump, with the needle 328 is accomplished in part through a valve 358, which forms part of the upper body 336 and selectively accesses either the needle 328 or a passage 340 to the inner chamber 320. In particular, the valve 358 selectively connects a same tubing 338 to either the needle 328 or the inner chamber 320 at one end and a remote pumping source such as one or more syringes or infusion pumps at the other end through one or more suitable connectors, in particular one or more y-connectors or remote valves positioned away from the upper body 336. Accordingly, a liquid medication can pass through the valve 358, through the needle 328 and into the patient.

In contrast, FIG. 3D depicts an expanded or deployed state, characterized as having the tip of the needle 328 at or above the bottom most plane of the lower body 344 such that the medical profession is protected from needle stick. For completeness, FIG. 3A depicts the medical device 300 transitioning from the collapsed state of FIG. 3B to the expanded state of FIG. 3D by selecting the valve 358 to access the inner chamber 320 and filling the chamber 320 with a fluid. The chamber 320 can be further guided upward through the addition of an external mechanical guide positioned outside of the collapsible sidewall 326 that upwardly guides the upper body 336 from lower body 344 during expansion thereby further reducing wobble of the upper body 336 and thus needle 328 during expansion of the chamber 320. The external mechanical guide can be joined at the lower end to the lower body 344 and at the upper end to the upper body 336.

It is notable that the two channels, 334, 340, do not intersect in the upper body 336. That is, the first channel 334 and the second channel 340 do not directly, fluidly communicate with one another within the upper body 336 due to the valve 358. In the collapsed state (FIG. 3B), the first channel 334 is connected to the needle 328 to infuse medication directly into the patient.

The device 300 can be formed from materials and manufacturing methods known to those in the medical device field. For instance, the upper body 336 and lower body 344 may be formed using conventional injection molding techniques with suitable polymers used in the formation of many medical devices such as polypropylenes of other suitable polymers. Similarly, the sidewall 326 of the chamber 320 may be formed from rubber or foldable polymer then adhered or fused to the upper body 336 and lower body 344. The pierceable barrier 346 may be formed from self-sealing silicone rubber. The lower body 344 may be provided with an aperture that is covered or filled with polymer or silicone to form the pierceable barrier 346. Alternatively, the lower body 344 may itself be formed, at least in part, from a pierceable material, such as a self-sealing polymer or silicone to form the pierceable barrier 346.

This embodiment exemplifies features that may also be incorporated into other embodiments, namely, a rotating valve 358 that forms part of the upper body 336 and selectively delivers fluid to either the needle 328 or the chamber 320 from a same tubing 338 thereby permitting the user to selectively deliver fluid to either the needle 328 or the chamber 320 through rotation of a handle 360, which is typically a 180 degree rotation. Thus, operation of the infusion device 300 would typically include rotating the handle 360. Closing the valve 358 can be accomplished by about 45 to 135 degree rotation of the handle 360 to prevent access to both channels 334, 340.

Accordingly, use of the device shown in FIGS. 3A-D can provide a method of delivering medication into or through an implanted medical port, which includes providing the infusion device 300 in a collapsed configuration with the valve 358 designating fluid communication with the needle 328, aligning the needle 328 with an implanted infusion port, and pressing the infusion device 300 such that needle 328 pierces the patient's skin, then into the septum of the implanted port. To further assist with insertion or handling, the uppermost portion of the upper body 336, or a portion of the lower body 344 may be flattened, convex, concave, flanged, curved or suitably shaped to accept a hand or finger to assist in securely gripping or pressing the infusion device 300. Once the needle 328 pierces the skin and is inserted into the patient's infusion port, the lower body 344 can be adhesively mounted to the patient through the use of adhesive mounts positioned along the underside of the lower body 344 or by applying tape over outward extending flanges of the lower body 344. Infusion of a medical sample is accomplished by delivering the sample into the first channel 334, which is fluidly coupled to the needle 328, and thus implanted infusion port.

After infusion is complete, the upper body 336 is rotated in relation to the lower body 344 such that the interlocking structures 356a, 356b are released. The handle 360 is rotated to designate fluid connection with the inner chamber 320. A fluid is introduced into the expandable chamber 320 via the same tubing 338 to initiate volumetric chamber 320 filling and upward extension of the chamber sidewall 326. The skilled artisan will appreciate that the fluid may be any suitable fluid such as water, saline, phosphate buffered saline, wash solution, bleach solution or other liquids. Alternatively, compressed gas, such as compressed air, can be applied to the chamber 320. Preferably, fluid is continually introduced at least until the needle 328 is withdrawn from the port, and until the bevel or tip of the needle 328 is at or above the lowermost plane of the lower body 344. In the expanded or deployed state the needle 328 may remain captured within the pierceable barrier 346, which acts to seal the bottom of the chamber 320. Alternatively, the bevel or tip of the needle 328 may be captured entirely within the chamber 320 and away from the piercable barrier 346. The device 300 is then removed from the patient. The chamber 320 is therefore a closed system defined by the piercable barrier 346 and selection of the valve 358 in a closed state. Further protection against needle stick can be accomplished by providing a blocking structure configured to block access entirely through the piercable barrier 346 by the needle 328 upon expansion.

Figure 4A:
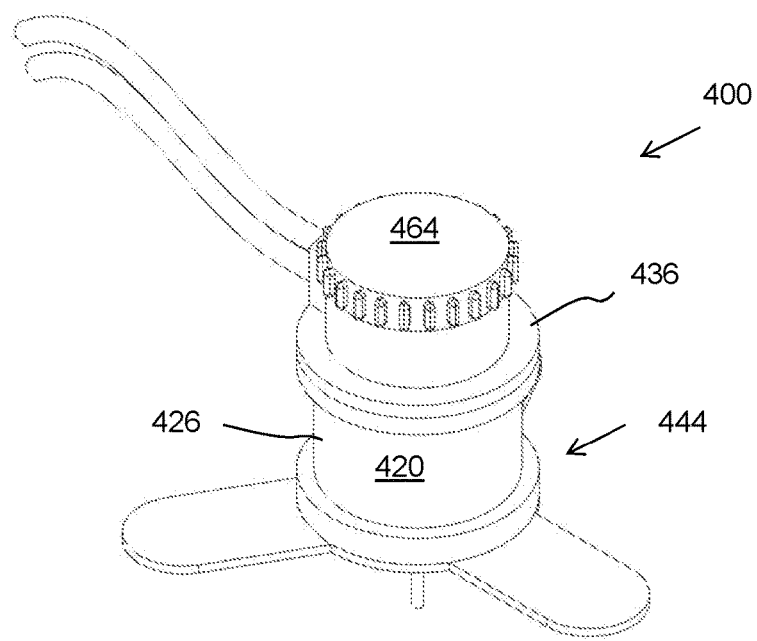
FIGS. 4A-D depict an infusion device showing an exemplary valve mechanism to selectively deliver fluid into different channels of the device from different tubing.
Figure 4B:
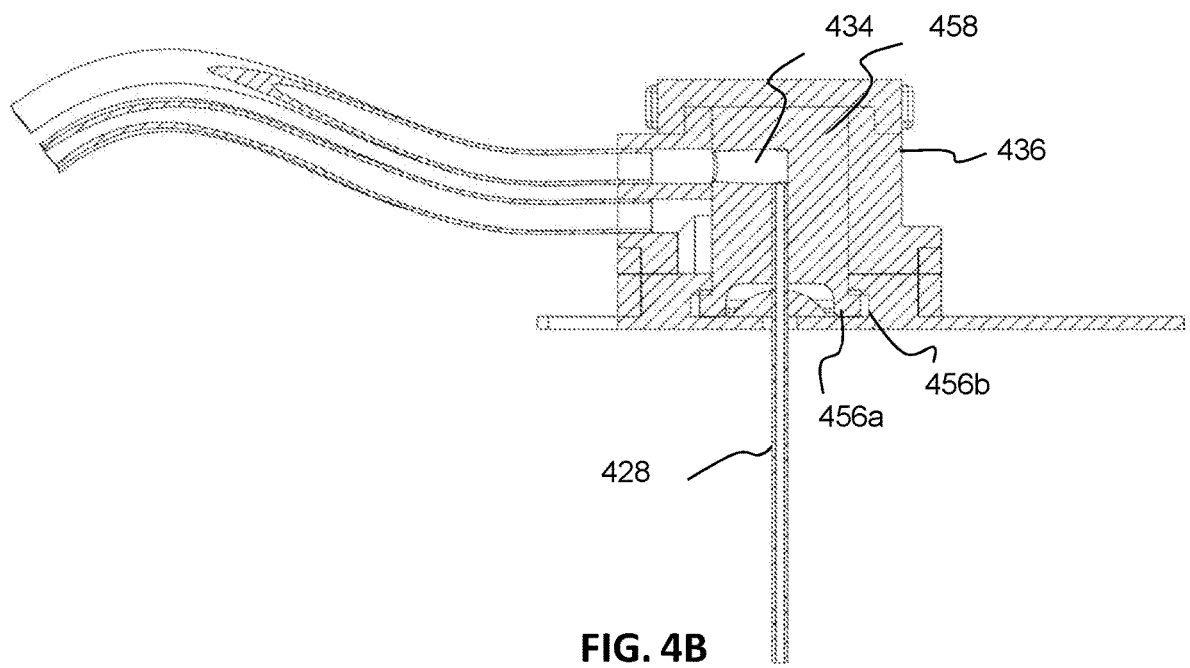
Figure 4C:
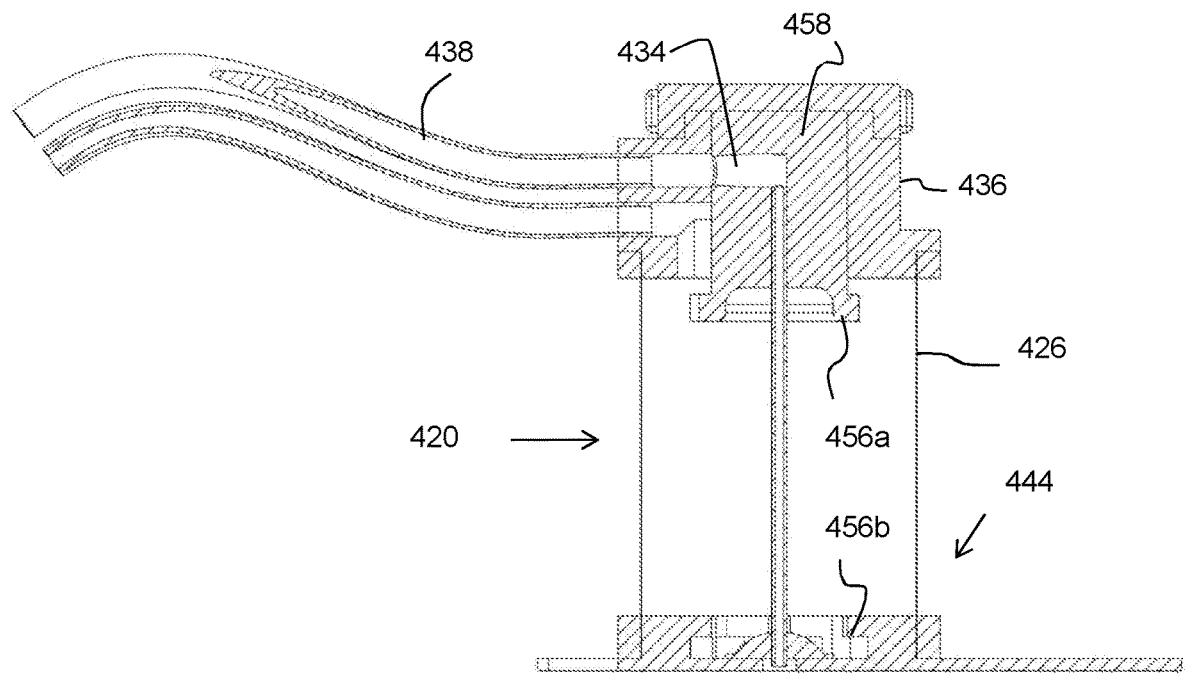
Figure 4D:
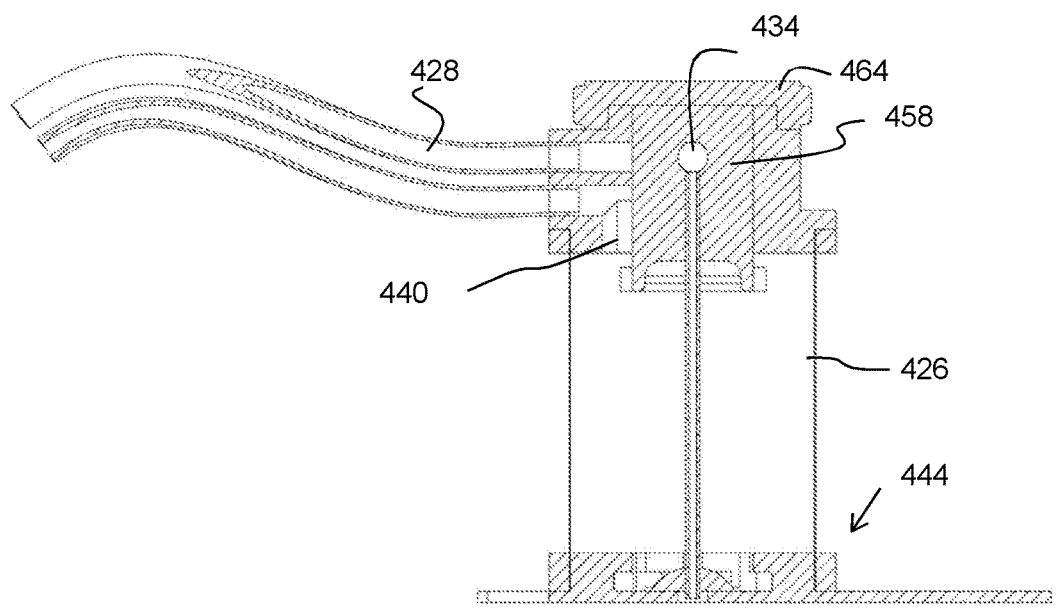

In another related embodiment shown in FIGS. 4A-D, a medical infusion device 400, is provided, which includes a chamber 420 having an upper body 436, a sidewall 426, and a lower body 444, characterized in that the chamber 420 has a collapsed state (FIG. 4B with sidewall 426 removed for viewing simplicity) and an expanded state (FIGS. 4C, 4D). The skilled artisan would appreciate that the lower body 444 could be divided into a mounting base with lower body insert more akin to FIG. 1 if desired. As shown in FIG. 4B, the collapsed state is further characterized as having a needle 428, preferably a non-coring or Huber needle affixed to the upper body 436, passing through the lower body 444 and thus being capable of accessing a patient's implanted medical port. Fluid connection between a remote source, including but not limited to a syringe or infusion pump, and the needle 428 is accomplished in part through an integrated valve 458 that selectively prevents or permits access to a first channel 434 within an upper body 436, which itself is positioned at the upper end of the chamber 420. In particular, the first channel 434 of the upper body 436 is fluidly connected to the needle 428 and can be fluidly coupled to tubing 428 by the appropriate valve 458 position, thereby permitting infusion from a remote pumping source such as the syringe or infusion pump. Accordingly, a liquid medication can pass across the valve 458, through the first channel 434, through the needle 428 and into the patient.

In contrast, FIGS. 4C, 4D depict a volumetrically expanded state (also referred to as a deployed state), characterized as having the bevel or tip of the needle 428 at or above the bottom most plane of the lower body 444. For completeness, FIG. 4A depicts the medical device 400 transitioning from the collapsed state of FIG. 4B to the expanded state of FIGS. 4C, 4D by filling the chamber 420 with a fluid through a second channel 440 within the upper body 436. The chamber 420 can be further guided upward through the addition of an external mechanical guide positioned outside of the collapsible sidewall 426 that upwardly guides the upper body 436 from the lower body 444 during expansion thereby further reducing wobble of the upper body 436 and thus needle 428 during expansion of the chamber 420. The external mechanical guide can be joined at the lower end to the lower body 444 and at the upper end to the upper body 436.

It is notable that the two channels, 434, 440, do not intersect in the upper body 436. That is, the first channel 434 and the second channel 440 do not directly, fluidly communicate with one another within the upper body 436. In the collapsed state (FIG. 4B), the first channel 434 is connected to the needle 428 to infuse medication directly into the patient. In the expanded state (FIGS. 4C, 4D), preventing the intersection between the first channel 434 and second channel 440 within the upper body 436 provides a mechanism to retract the needle using hydraulic pressure.

The device 400 can be formed from materials and manufacturing methods known to those in the medical device field. For instance, the upper body 436 and lower body 444 may be formed using conventional injection molding techniques with suitable polymers used in the formation of many medical devices such as polypropylenes or other polymers. Similarly, the sidewall 426 of the chamber 420 may be formed from rubber or foldable polymer then adhered or fused to the upper body 436 and lower body 444. The pierceable barrier 446 may be formed from resealable silicone rubber. The lower body 444 may be provided with an aperture that is covered or filled with polymer or silicone to form the pierceable barrier 446. Alternatively, the lower body 444 may itself be formed, at least in part, from a pierceable material, such as a self-sealing polymer or silicone to form the pierceable barrier 446.

This embodiment exemplifies features that may also be incorporated into other embodiments, namely, a rotating valve 458 that forms part of the upper body 436 that selectively prevents or permits fluid delivery through the needle 428, and interlocking structures 456a, 456b that are rubber protrusions and corresponding recesses for detachment or release by chamber 420 filling. Thus, operation of the infusion device 400 would typically include rotating the handle 460 to open or close the valve 458 and releasing the interlocking structures 456a, 456b in response to increasing fluid pressure during chamber 420 filling.

Accordingly, use of the device as shown in FIGS. 4A-D can provide a method of delivering medication into or through an implanted medical port, which includes providing the infusion device 400 in a collapsed configuration, selecting the valve 458 to fluidly connect with the needle 428, aligning the needle 428 with an implanted infusion port, and pressing the infusion device 400 such that the needle 428 pierces the patient's skin, then into the septum of the implanted port. To further assist with insertion or handling, the uppermost portion of the upper body 436, or a portion of the lower body 444 may be flattened, convex, concave, flanged, curved or suitably shaped to accept a hand or finger to assist in securely gripping or pressing the infusion device 400. Once the needle 428 pierces the skin and is inserted into the patient's infusion port, the lower body 444 can be adhesively mounted to the patient through the use of adhesive mounts positioned along the underside of the lower body 444 or by applying tape over outward extending flanges of the lower body 444. Infusion of a medical sample is accomplished by delivering the sample through the valve 458, through first channel 434, which is fluidly coupled to the needle 428, and into the implanted infusion port.

After infusion is complete, the handle 464 is rotated so that the valve 458 designates fluid connection with the inner chamber 420. A fluid is introduced into the expandable chamber 420 to initiate volumetric chamber 420 filling and upward extension of the chamber sidewall 426, which overcomes the holding force of the rubber protrusions. The skilled artisan will appreciate that the fluid may be any suitable fluid such as water, saline, phosphate buffered saline, wash solution, bleach solution or other liquids. Alternatively, compressed gas, such as compressed air, can be applied to the chamber 420. Preferably, fluid is continually introduced at least until the needle 428 is withdrawn from the port, and until the bevel or tip of the needle 428 is at or above the lowermost plane of the lower body 444. In the expanded or deployed state the needle 428 may remain captured within the piercable barrier 446, which acts to seal the bottom of the chamber 420 and retain the fluid.

Alternatively, the needle can be raised such that the bevel or tip is housed within the chamber 420. The device 400 is then removed from the patient. Continued flow of solution into the chamber would then backflush the needle 428, the first channel 434 and the tubing 438. As with the embodiments above, a visual indicator may be employed to monitor backflushing to ensure removal of potentially hazardous medication or solution and therefore may notify the user when the device 400 may be disposed of without special designation as a hazardous material. Further protection against needle stick can be accomplished by providing a blocking structure configured to block access entirely through the piercable barrier 426 by the needle 428 upon expansion.

Figure 5A:
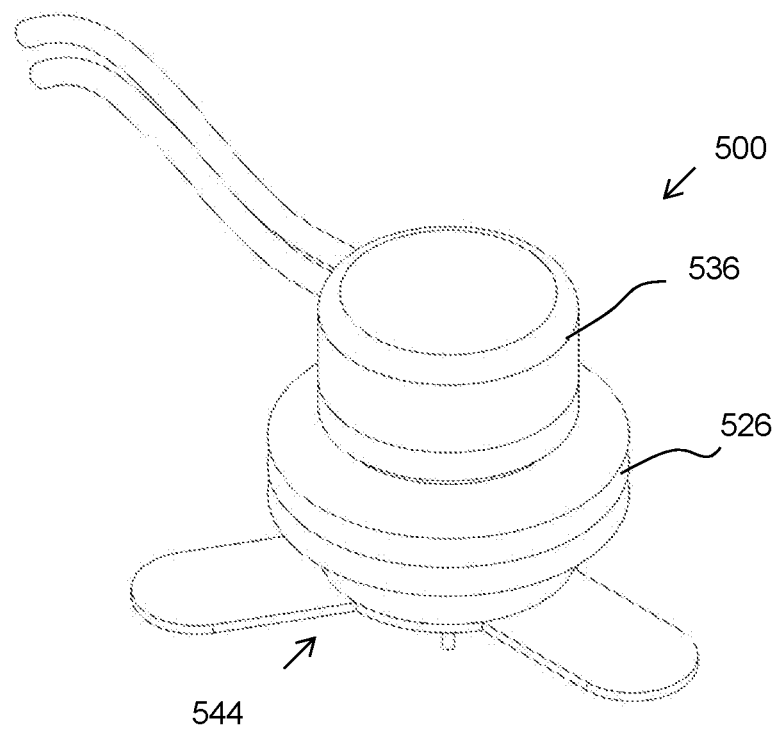
FIGS. 5A-F depict an infusion device showing an exemplary volumetric expansion of a chamber having a sidewall in a bellows configuration and use of a friction fit locking mechanism.
Figure 5B:
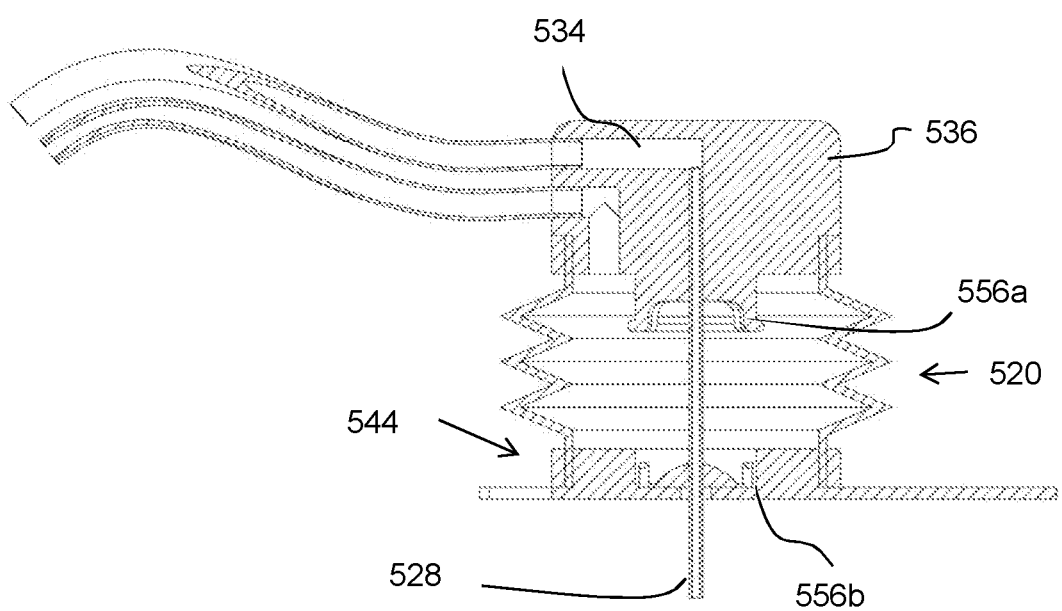
Figure 5C:
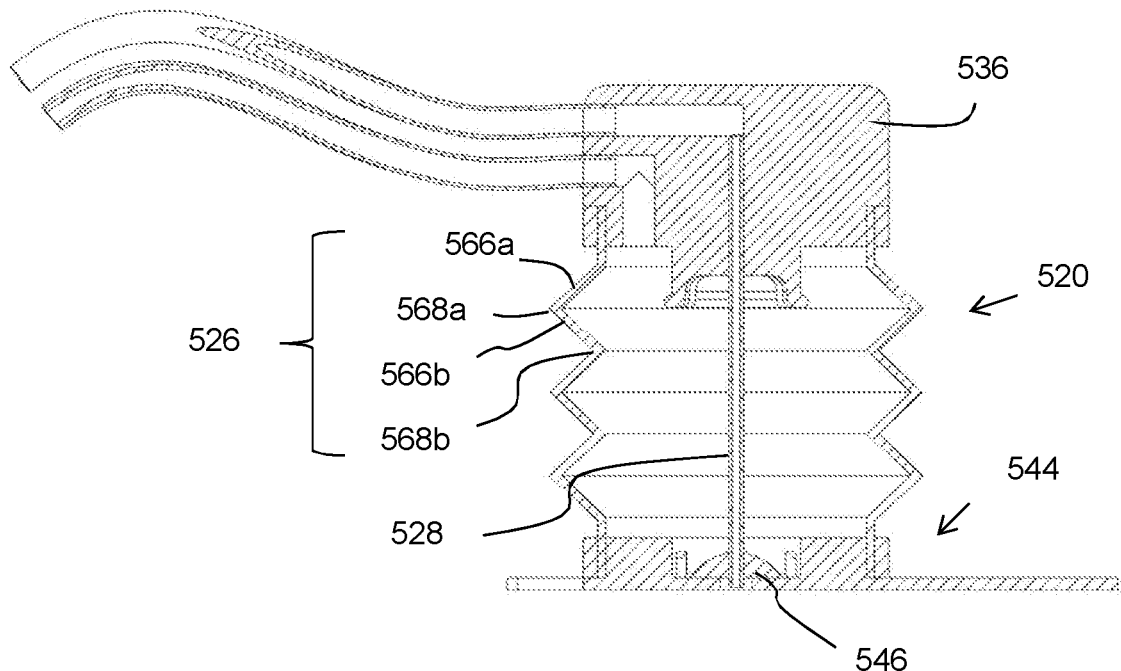
Figure 5D:
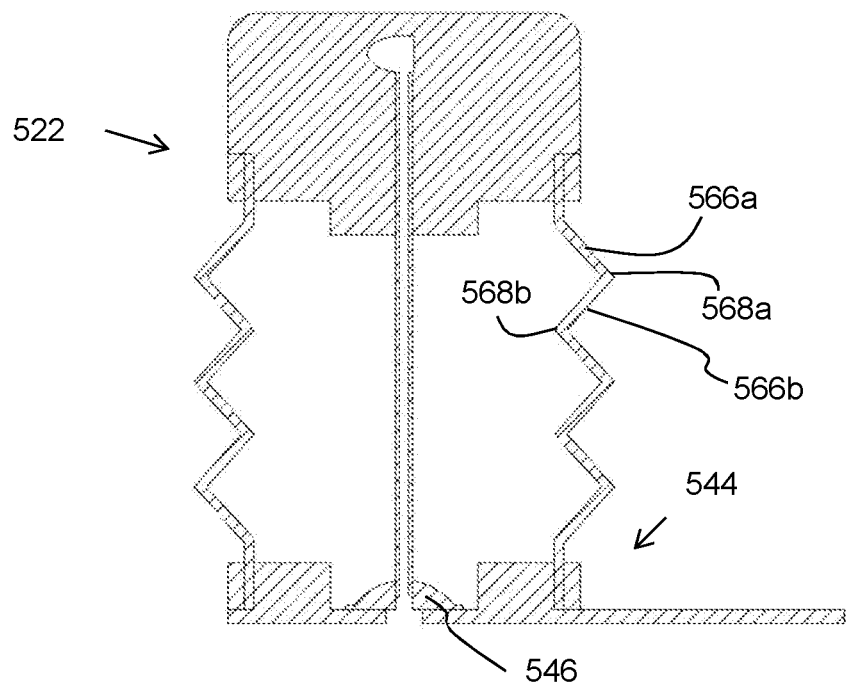
Figure 5E:
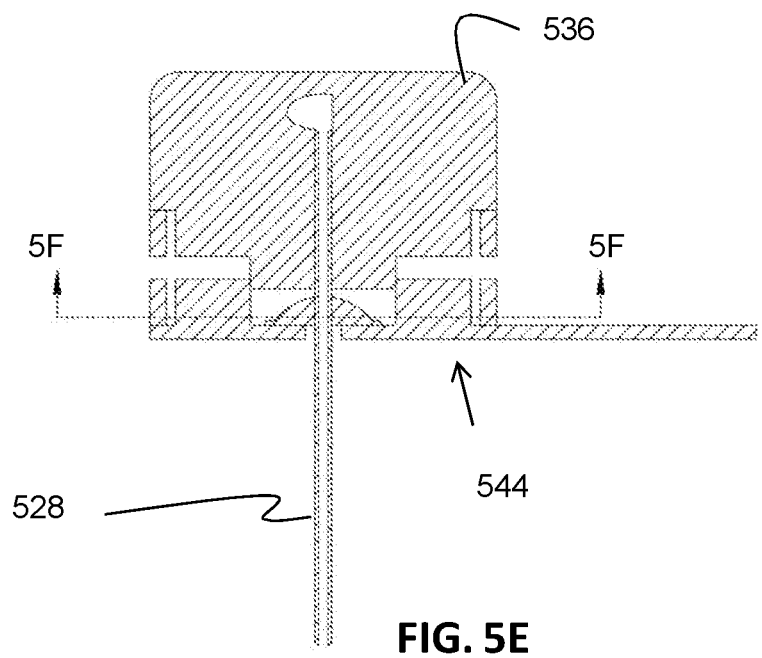
Figure 5F:
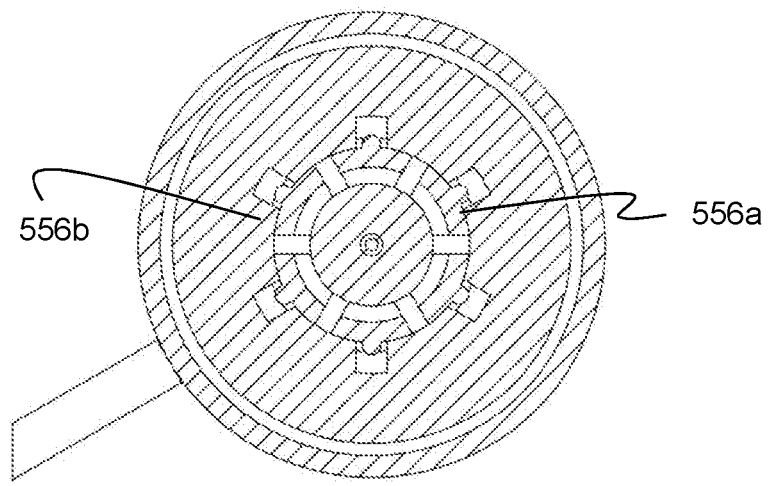

In another related embodiment shown in FIGS. 5A-E, a medical infusion device 500, is provided, which includes a chamber 520 defined by an upper body 536a sidewall 526, and a lower body 544, characterized in that the chamber 520 has a collapsed state (FIG. 5B) and an expanded state (FIGS. 5C, 5D). The skilled artisan would appreciate that the lower body 544 could be divided into a mounting base with lower body insert more akin to FIG. 1 if desired. As shown in FIG. 5B, the collapsed state is further characterized as having a needle 528, preferably a non-coring or Huber needle affixed to the upper body 536, passing through the lower body 544 and thus being capable of accessing a patient's implanted medical port. Fluid connection between a remote source, including but not limited to a syringe or infusion pump, and the needle 528 is accomplished in part through a first channel 534 within an upper body 536, which itself is positioned at the upper end of the chamber 520. In particular, the first channel 534 of the upper body 536 is fluidly connected to the needle 528 and can be fluidly coupled to tubing 538 thereby permitting infusion from a remote pumping source such as the syringe or infusion pump. Accordingly, a liquid medication can pass across through the first channel 534, through the needle 528 and into the patient.

In contrast, FIGS. 5C-5D depict an expanded state (also referred to as a deployed state), characterized as having the bevel or tip of the needle 528 at or above the bottom most plane of the lower body 544. Transition from a collapsed state to an expanded or deployed state occurs by filling the chamber 520 with a fluid through a second channel 540 within the upper body 536. The chamber 520 can be further guided upward through the addition of an external mechanical guide positioned outside of the collapsible sidewall 526 that upwardly guides the upper body 536 from the lower body 544 during expansion thereby further reducing wobble of the upper body 536 and thus needle 528 during expansion of the chamber 520. The external mechanical guide can be joined at the lower end to the lower body 544 and at the upper end to the upper body 536.

It is notable that the two channels, 534, 540, do not intersect in the upper body 536. That is, the first channel 534 and the second channel 540 do not directly, fluidly communicate with one another within the upper body 536. In the collapsed state (FIG. 5B), the first channel 534 is connected to the needle 528 to infuse medication directly into the patient. In the expanded state (FIG. 5C), preventing the intersection between the first channel 534 and second channel 540 within the upper body 536 effectively cleans the outside and inside surfaces of the needle 528 from hazardous bloodborne pathogens and toxic medications to protect the user. In particular, by avoiding intersection between the two channels 534, 540 in the upper body 536, wash solution pumped into the second channel 540 passes around and through the needle 528 before passing through the first channel 534 to exit the device 500.

The device 500 can be formed from materials and manufacturing methods known to those in the medical device field. For instance, the upper body 536 and lower body 544 may be formed using conventional injection molding techniques with suitable polymers used in the formation of many medical devices such as polypropylenes or other polymers. Similarly, the sidewall 526 of the chamber 520 may be formed from rubber or foldable polymer then adhered or fused to the upper body 536 and lower body 544. The piercable barrier 546 may be formed from resealable silicone rubber. The lower body 544 may be provided with an aperture that is covered or filled with polymer or silicone to form the piercable barrier 546. Alternatively, the lower body 544 may itself be formed, at least in part, from a piercable material, such as a self-sealing polymer or silicone to form the piercable barrier 546.

This embodiment exemplifies features that may also be incorporated into other embodiments, namely, bendable detent connectors 556a, 556b to ensure the chamber 520 remains in a collapsed state during infusion of a medical sample. Further, the collapsible sidewall 526 of the chamber 520 is provided in a bellows configuration, where a series of segments 566a, 566b between alternating folds 568a, 568b are foldable like an accordion in a predetermined or bellows-like configuration. In the bellows-like configuration the segments 566a, 566b between folds 568a, 568b can be rigid, flexible or bendable; however, the chamber sidewall 526 should fold at the predetermined fold lines 568a, 568b.

Accordingly, use of the device as shown in FIGS. 5A-E can provide a method of delivering medication into or through an implanted medical port, which includes providing the infusion device 500 in a collapsed configuration, aligning the needle 528 with an implanted infusion port, and pressing the infusion device 500 such that needle 528 pierces the patient's skin, then into the septum of the implanted port. To further assist with insertion or handling, the uppermost portion of the upper body 536, or a portion of the lower body 544 may be flattened, convex, concave, flanged, curved or suitably shaped to accept a hand or finger to assist in securely gripping or pressing the infusion device 500. Once the needle 528 pierces the skin and is inserted into the patient's infusion port, the lower body 544 can be adhesively mounted to the patient through the use of adhesive mounts positioned along the underside of the lower body 544 or by applying tape over outward extending flanges of the lower body 544. Infusion of a medical sample is accomplished by delivering the sample through the first channel 534, which is fluidly coupled to the needle 528, and into the implanted infusion port.

After infusion is complete, a fluid is introduced into the expandable chamber 520 to initiate chamber 520 filling, release of the bendable detent connectors 556a, 556b, and upward extension of the chamber sidewall 526. The skilled artisan will appreciate that the fluid may be any suitable fluid such as water, saline, phosphate buffered saline, wash solution, bleach solution or other liquids. Alternatively, compressed gas, such as compressed air, can be applied to the chamber 520. Preferably, fluid is continually introduced at least until the needle 528 is withdrawn from the port, and until the bevel or tip of the needle 528 is at or above the lowermost plane of the lower body 544. In the expanded or deployed state the needle 528 may remain captured within the pierceable barrier 546, which acts to seal the bottom of the chamber 520. Alternatively, the needle can be raised such that the bevel or tip is housed within the chamber 520. The device 500 is then removed from the patient. Continued flow of solution into the chamber would then backflush the needle 528, the first channel 534 and the tubing 538. As with the embodiment above, a visual indicator may be employed to monitor backflushing to ensure removal of potentially hazardous medication or solution and therefore may notify the user when the device 500 may be disposed of without special designation as a hazardous material. Further protection against needle stick can be accomplished by providing a blocking structure configured to block access through the pierceable barrier 546 by the needle 528 upon expansion.

Figure 6A:
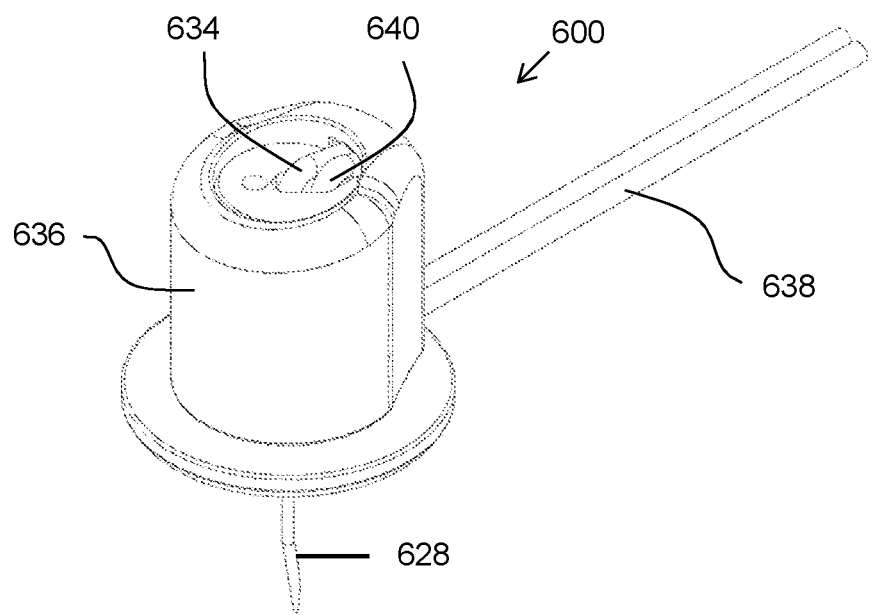
FIGS. 6A-J depict an infusion device showing exemplary volumetric expansion of a chamber having a bellows configuration that overcomes friction fit attachment of the upper body, lower body and base together with needle sheathing and needle capture approaches.
Figure 6B:
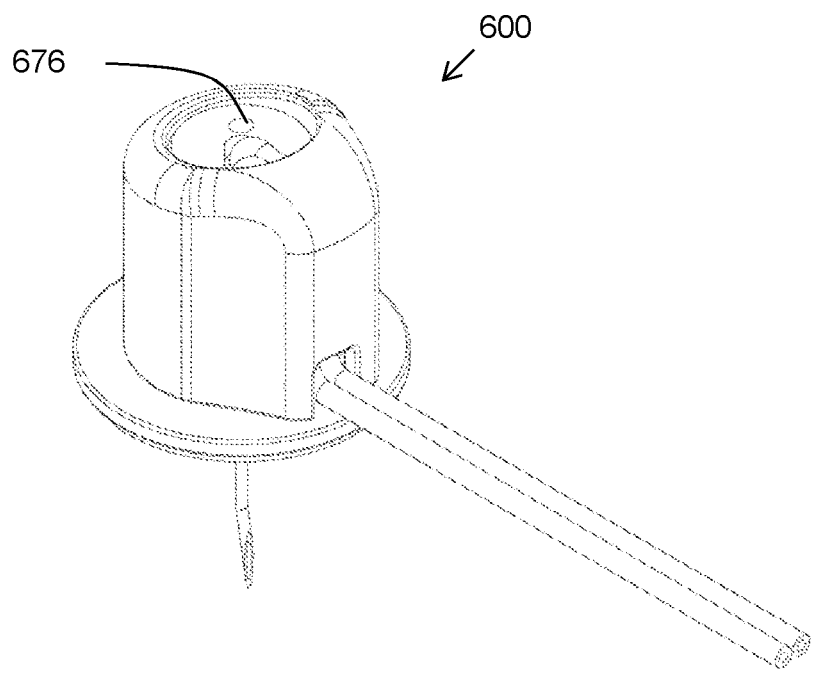
Figure 6C:
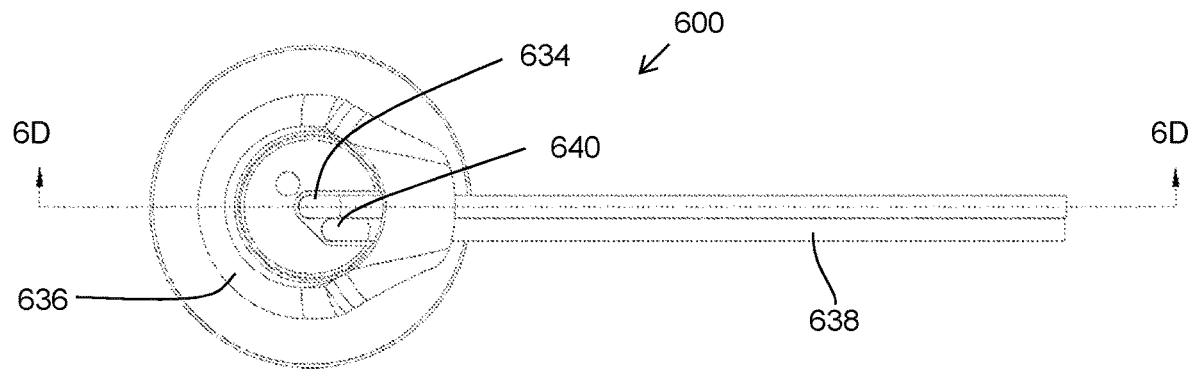
Figure 6D:
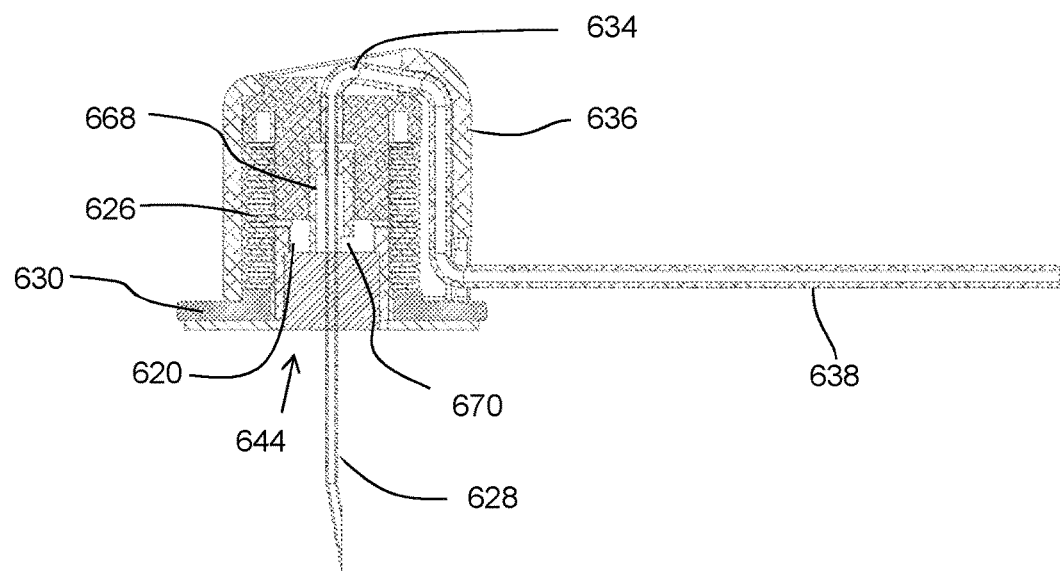
Figure 6E:
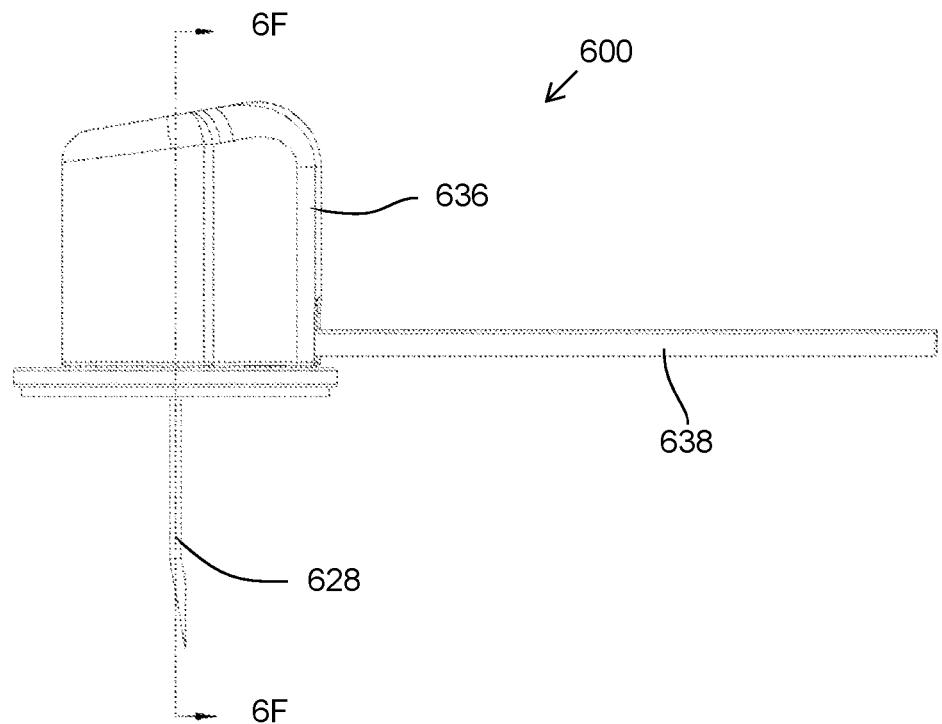

In another related embodiment shown in FIGS. 6A-J, a medical infusion device 600, is provided, which includes a chamber 620 having an upper body 636, a sidewall 626, and a lower body 644, shown releasably friction fit to a mounting base 630, characterized in that the chamber 620 has a collapsed state (FIGS. 6A-F) and an expanded state (FIGS. 6G-J). The lower body 644 could be formed as a single unit with the mounting base 630 if selective release of the chamber 620 is from a base 630 is not desired. As shown in FIG. 6D, the collapsed state is further characterized as having a needle 628, preferably a non-coring or Huber needle affixed to the upper body 636, passing through the lower body 644 and thus capable of accessing a patient's implanted medical port. Although the device 600 is preferably provided in the collapsed state, collapsing the device 600 can involve downwardly pushing the upper body 636 against the lower body 644. A hydrophobic filter 676 in a through passage into the chamber 620 may allow air to escape from the chamber 620 while collapsing the chamber 620. Fluid connection between a remote source, including but not limited to a syringe or infusion pump, and the needle 628 is accomplished in part through a first channel 634 within an upper body 636, which itself is positioned at the upper end of the chamber 620. In particular, the first channel 634 of the upper body 636 acts as a conduit to fluidly connect the lumen of the needle 628 to tubing 638 thereby permitting infusion from a remote pumping source such as the syringe or infusion pump through the needle 628. Accordingly, a liquid medication can pass through the first channel 634, through the needle 628 and into the patient's implanted port.

Figure 6F:
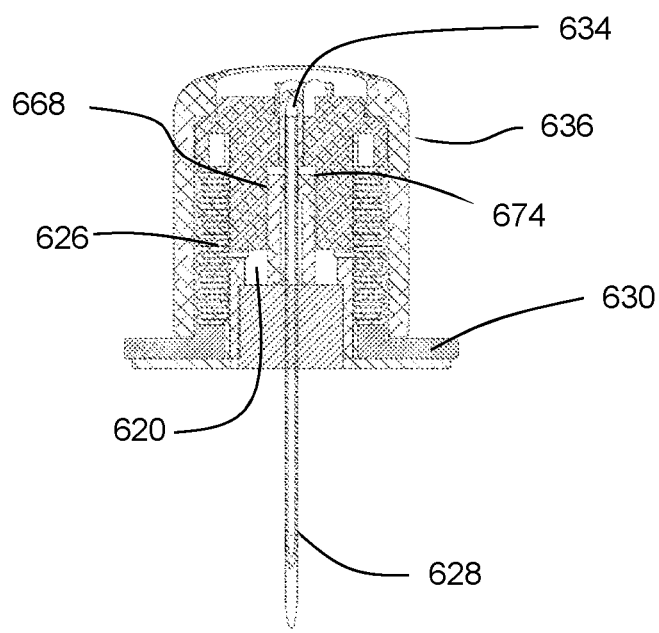
Figure 6G:
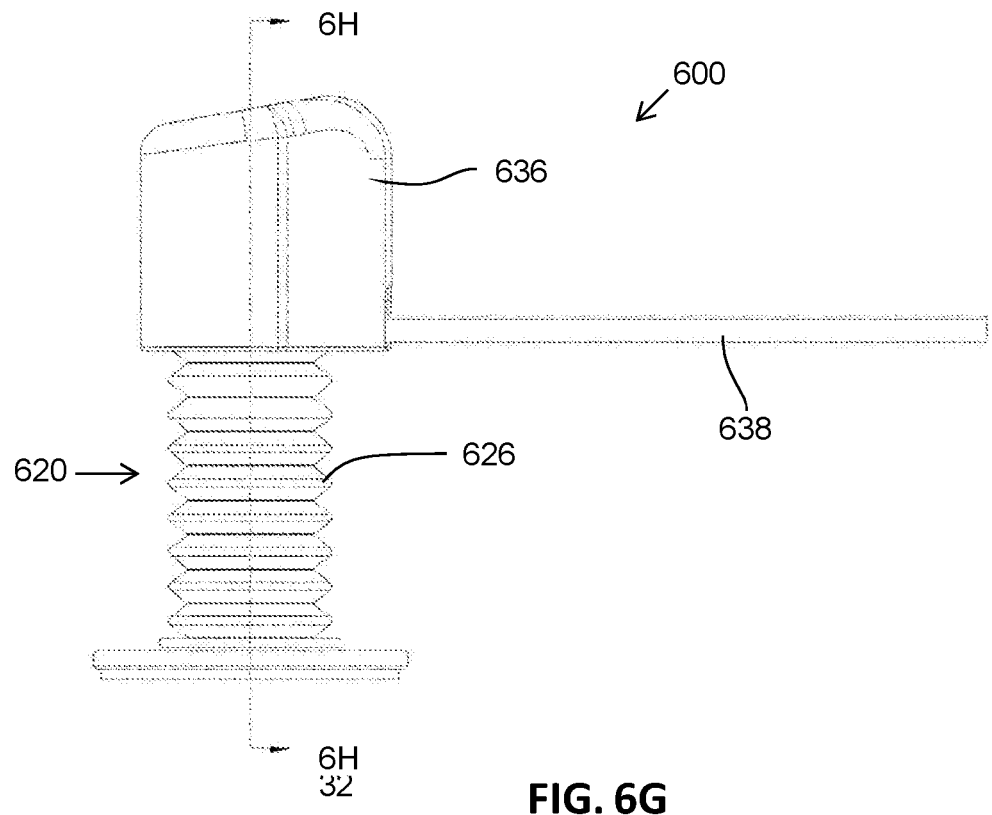
Figure 6H:
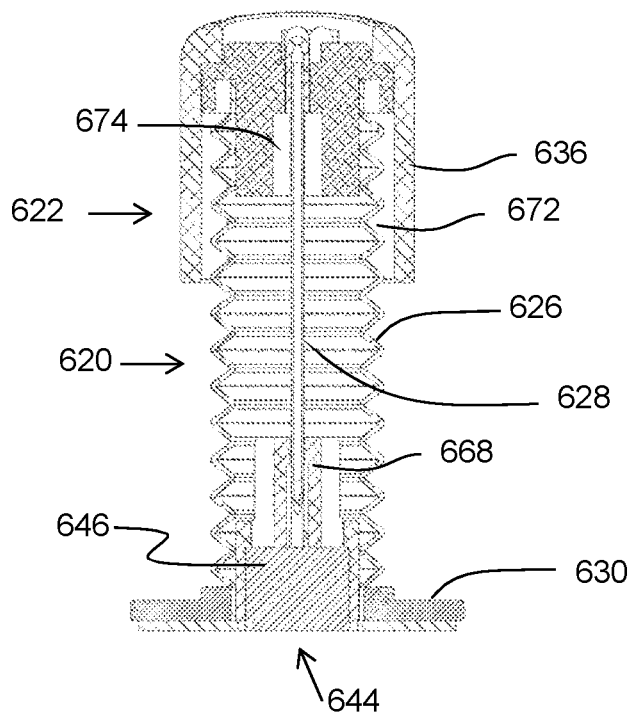
Figure 6I:
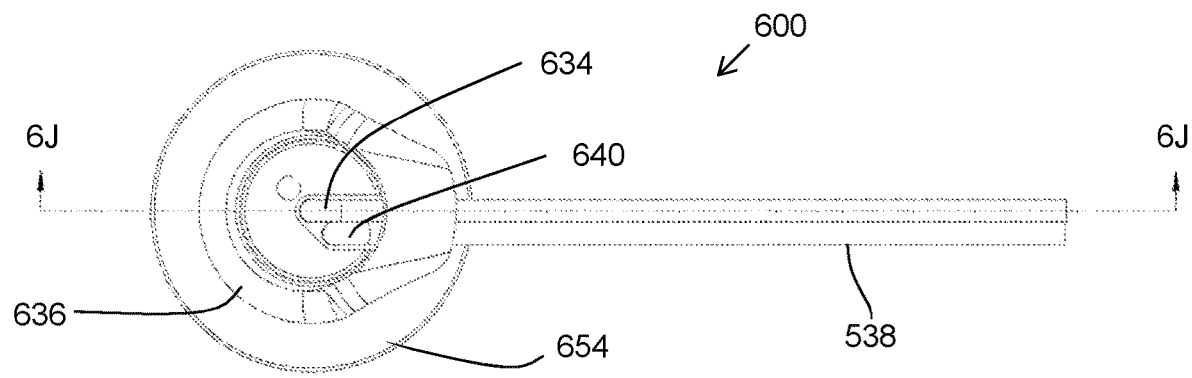
Figure 6J:
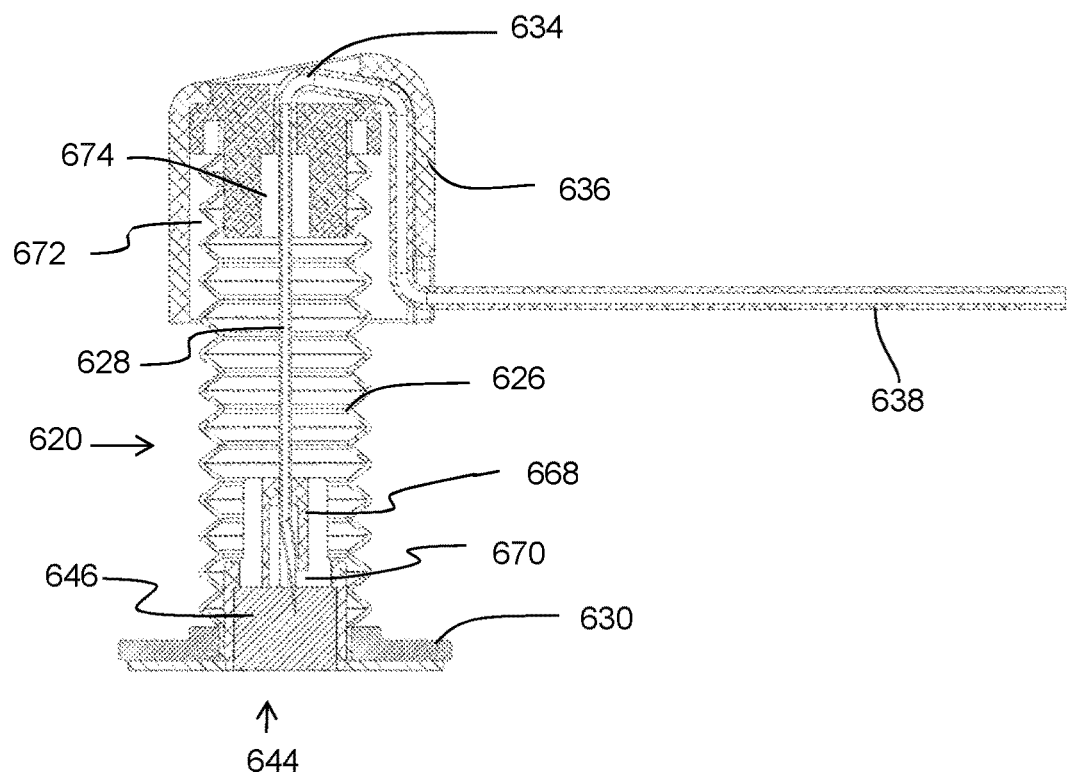

In contrast, FIG. 6H depicts an expanded or deployed state, characterized as having the bevel or tip of the needle 628 at or above the bottom most plane of the lower body 644 and preferably either securely held in the pierceable barrier 646 as shown in FIG. 6J or housed within the chamber 620 as shown in FIG. 6H. As shown in FIGS. 6D, 6F, 6G, a tubular sheath 668 forms part of the lower body 644 of the chamber 620 and extends upward at least partially along the height of the chamber 620 acting as a guiding structure to further guide and retain the needle 628 in proper linear alignment during deployment of the infusion device 600 and may act to sheathe the bevel or tip of the needle 628 when entirely captured by the chamber 620 as shown in FIG. 6H. The sheath 668 may also be provided with an access port 670 to more efficiently fluidly access a sheathed needle 628 by fluid contents of the chamber 620. Transitioning from a collapsed state to an expanded or deployed state occurs by filling the chamber 620 with a fluid through a second channel 640 acting as a conduit through the upper body 636. The chamber 620 can be further guided upward through the addition of an external mechanical guide positioned outside of the collapsible sidewall 626, preferably having an end of travel release, that upwardly guides the upper body 636 from the base 630 during expansion thereby further reducing wobble of the upper body 636 and thus needle 628 during expansion of the chamber 620. The external mechanical guide can be joined at the lower end to the base 630 and at the upper end to the upper body 636. Upon expansion of the chamber 620, preferably the mechanical guide releases the upper body 636 from the base 630 thereby releasing the chamber 620 with needle 628.

It is notable that the two channels, 634, 640, do not intersect in the upper body 636. That is, the first channel 634 and the second channel 640 do not directly, fluidly communicate with one another within the upper body 636. In the collapsed state (FIGS. 6A-F), the first channel 634 is connected to the needle 628 to infuse medication directly into the patient. In the expanded state (FIGS. 6G-J), preventing the intersection between the first channel 634 and second channel 640 within the upper body 636 effectively cleans the outside and inside surfaces of the needle 628 from hazardous bloodborne pathogens and toxic medications to protect the user. In particular, by avoiding intersection between the two channels 634, 640 in the upper body 636, wash solution pumped into the second channel 640 passes around and through the needle 628 before passing through the first channel 634 to exit the device 600.

The device 600 can be formed from materials and manufacturing methods known to those in the medical device arts. For instance, the upper body 636, lower body 644, base 630 and sheath 668 may be formed using conventional injection molding techniques with suitably rigid polymers used in the formation of many medical devices, such as polypropylene or polymer. Similarly, the sidewall 626 of the chamber 620 may be formed from rubber or foldable polymer then adhered or fused to the upper body 636 and lower body 644. The pierceable barrier 646 may be formed from resealable silicone rubber. The lower body 644 may be provided with an aperture that is covered or filled with polymer or silicone to form the pierceable barrier 446, preferably in alignment with the sheath 668. Alternatively, the lower body 644 may itself be formed, in part, from a pierceable material, such as a self-sealing polymer or silicone to form the pierceable barrier 646. This embodiment exemplifies features that may also be incorporated into the other embodiments, namely, friction fit connection about the perimeter of the upper body 636 and the base 630 when the infusion device 600 is provided in the collapsed state. In addition, by providing an recess 674 in the upper body 636 for nesting the sheath 668 as shown in FIGS. 6D, 6H, further friction fit connection between the upper body 636 and the lower body 644 can be provided thereby eliminating the desire for additional locking structures to securely maintain the infusion device 600 in the collapsed state. In other embodiments, the recess 674 is spaced apart from the sheath 668 to avoid friction fitting. Still further, by forming a gap 672 between the upper body 636 that is sized to contact sidewall 626 of the chamber 620 when the infusion device 600 is in a compressed state, friction fitting between the upper body 636 and sidewall 626 can be achieved thereby further securing of the upper body 636 to the lower body 644. However, in some embodiments the gap 672 is sized to avoid contact with but instead only covers the sidewall 626.

Accordingly, use of the device as shown in FIGS. 6A-J can provide a method of delivering medication into or through an implanted medical port, which includes providing the infusion device 600 in a collapsed configuration, aligning the needle 628 with an implanted infusion port, and pressing the infusion device 600 such that needle 628 pierces the patient's skin, then into the septum of the implanted port. To further assist with insertion or handling, the upper body 636, or base 630 may be flattened, convex, concave, flanged, curved or suitably shaped to accept a hand or finger to assist in securely gripping or pressing the infusion device 600. Once the needle 628 pierces the skin and is inserted into the patient's infusion port, the base 630 is optionally adhesively mounted to the patient through the use of adhesive mounts positioned along the underside of the base 630 or by applying tape over an outward extending flange of the base 630. Infusion of a medical sample is accomplished by delivering the sample through the first channel 634, which is fluidly coupled to the needle 628, and into the implanted infusion port.

After infusion is complete, the upper body is pulled or fluid is introduced into the expandable chamber 620 to initiate chamber 620 filling at a sufficient force to overcome friction fit attachment between the upper body 636 and base 630 and optionally between the upper body 636, sheath 668 and sidewall 626, thereby unfolding the bellows and upwardly extending the chamber sidewall 626. The skilled artisan will appreciate that the fluid may be any suitable fluid such as water, saline, phosphate buffered saline, wash solution, bleach solution or other liquids. Alternatively, compressed gas, such as compressed air, can be applied to the chamber 620. Preferably, fluid is continually introduced at least until the needle 628 is withdrawn from the port, and until the bevel or tip of the needle 628 is at or above the lowermost plane of the lower body 644. In the expanded or deployed state the needle 628 may remain captured within the pierceable barrier 646, which acts to seal the bottom of the chamber 620. Alternatively, the needle can be raised such that the bevel or tip is housed within the chamber 620 and in particular sheathed by the sheath 668. Once the needle 628 is removed from the port, the device 600 releases. Continued flow of solution into the chamber can then pass through the access port 670 and backflush the needle 628, the first channel 634 and the tubing 638 as desired. As with the embodiments above, a visual indicator may be employed to monitor backflushing to ensure removal of potentially hazardous medication or solution and therefore may notify the user when the device 600 may be disposed of without special designation as a hazardous waste. In addition, further protection against needle stick can be accomplished by providing a blocking structure configured to block access through the pierceable barrier 646 by the needle 628 upon expansion of the chamber. Still further, the device 100 may include a remote valve along the tubing 638 to regulate flow into the needle 620 and/or into the chamber 620.

Figure 7A:
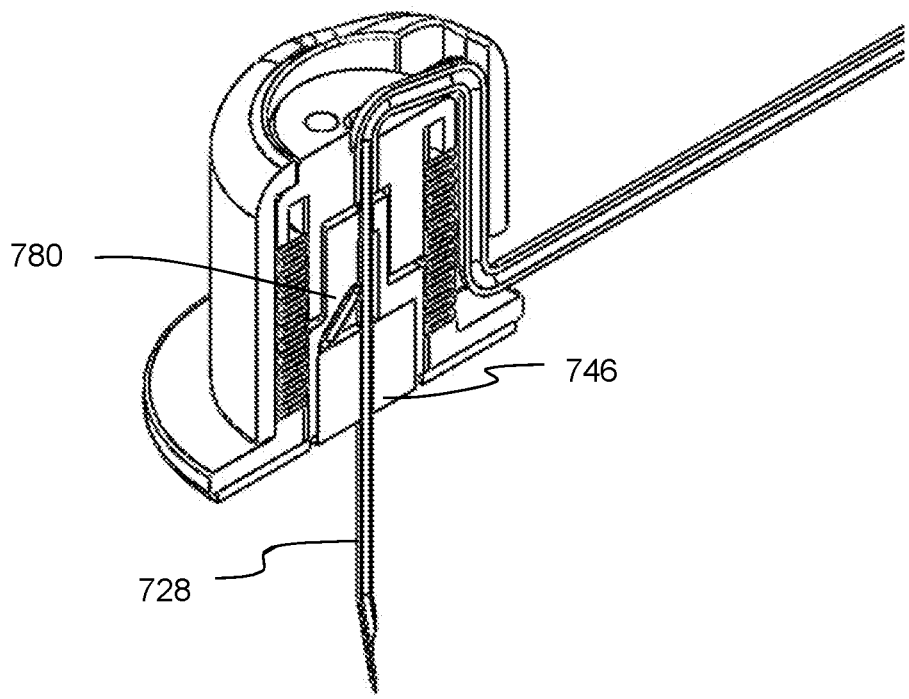
FIGS. 7A-B depict an infusion device with an exemplary blocking structure preventing the needle from piercing entirely through the pierceable barrier.
Figure 7B:
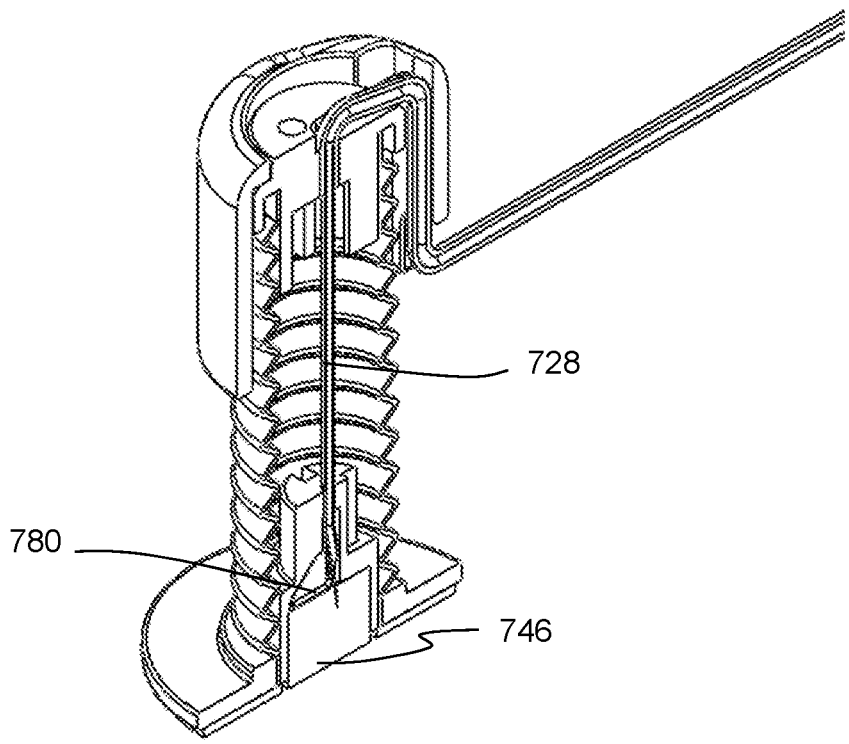

Embodiments above can incorporate a blocking structure to prevent the needle from traversing the entirety of the pierceable barrier after expansion of the chamber thereby further ensuring against needle stick injury and exposure to infusion samples. The blocking structure can be provided in a variety of configurations. In some embodiments, it is a material that is selectively presented between the tip of the needle and pierceable barrier, where the blocking structure is formed from a material that is not pierceable by the needle. Such structures can be suitably positioned for blocking during or at chamber expansion, such as but not limited by spring action, hinged, through the use of memory metals, or release from a suspended recess for positioning by gravitational forces. Such materials may be plastics of suitable formulation or thickness, metal, metal alloy or other materials that are not pierceable using forces conventionally used during insertion of a needle into a medical port. A related approach is shown in FIGS. 7A and 7B where a blocking structure 780 in the form of a jam lock is upwardly suspended by the needle 728 when in the collapsed configuration (FIG. 7A) and is configured to fall and jam or wedge against the needle 728 when in the expanded configuration (FIG. 7B), thereby preventing passage entirely across the pierceable barrier 746.

Figure 8A:
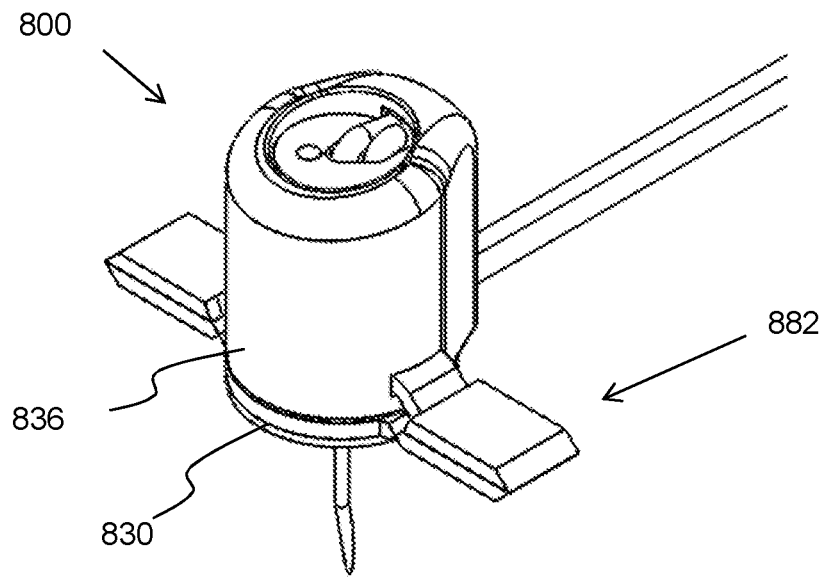
FIGS. 8A-B depict an infusion device with an exemplary external mechanical guide that upwardly guides the upper body from the base during expansion of the chamber and preferably releases the chamber after the end of travel.
Figure 8B:
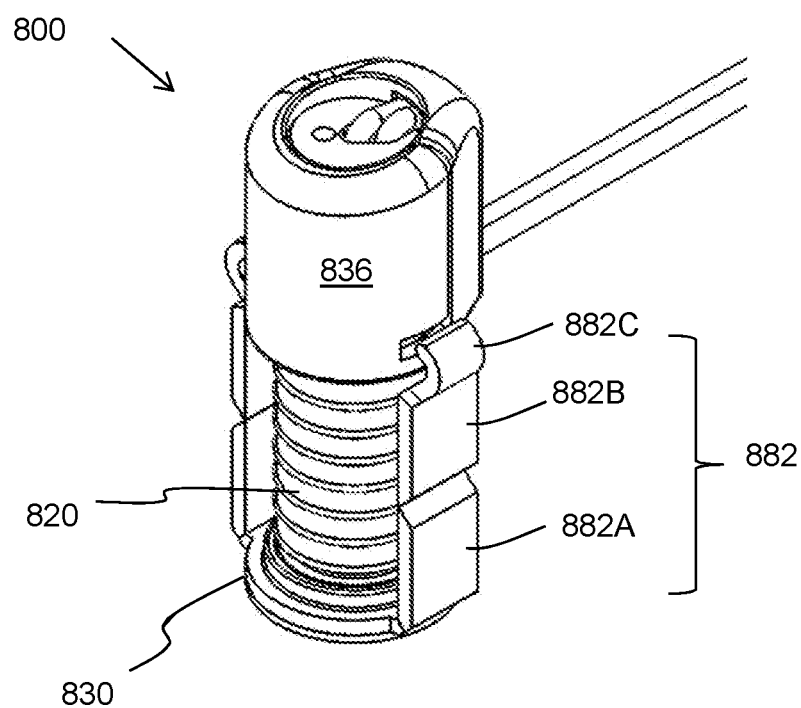

Embodiments herein can incorporate an external mechanical guide, preferably having an end of travel release, to further assist in upwardly guiding the upper body from the base during expansion of the chamber. This configuration further reduces the likelihood of the upper body and thus needle from wobbling during expansion. An exemplary external mechanical guide 882 is depicted in FIGS. 8A-B. Preferably there are two external mechanical guides 882 positioned at opposing sides of the device 800. Each mechanical guide 882 is preferably formed as two rigid segments 882A, 882B hinged at about the center to permit folding and unfolding thereby outwardly collapsing (FIG. 8A) and upwardly expanding (FIG. 8B) with the chamber 820. Preferably, the mechanical guide 882 is joined to the base 844 at one end, such as by gluing or injection molding, and is releasably joined to the upper body 836 at the opposing end, such as by a releasable hook 882C and complementary recess on the upper body 836. A hook 882C and recess configuration permits an end of travel release where the hook 882C rotates along the recess or slot until releasing when in the expanded state if desired. The mechanical guide 882 is typically formed from polymer plastic and narrowed at its center to form the hinge.

Figure 9A:
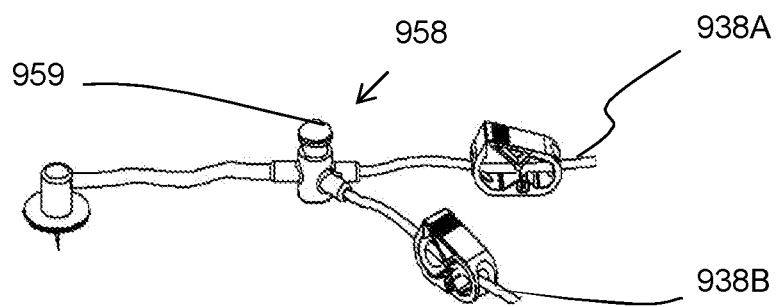
FIGS. 9A-B depict an infusion device showing an exemplary valve positioned remote from the upper body of the device.
Figure 9B:
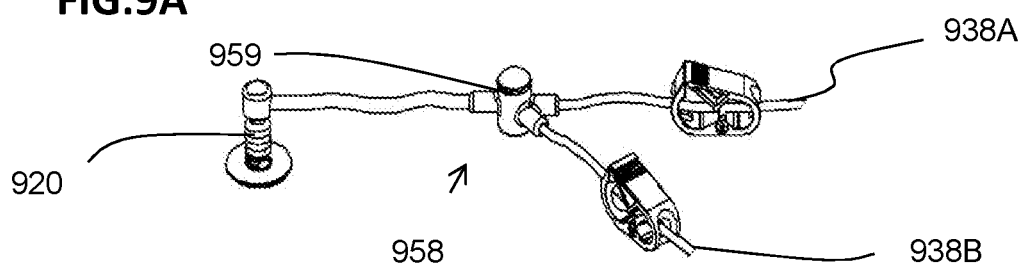

Each of the above embodiments herein can incorporate a valve positioned remote from the upper body for selectively connecting external sources to the chamber and/or needle. An exemplary configuration is shown in FIGS. 9A-B, where during the collapsed configuration (FIG. 9A), a remote valve 958 is selected to permit flow through a first line 938A, such as by presenting the valve 958 with an upward extending body 959; and during the expanded configuration (FIG. 9B), the valve 958 is selected, such as by pressing the body 959 downward, to permit flow through a second line 938B (coupled to a wash solution) to access the chamber 920 and backflush the needle and optionally first line 938A to remove residual infusion sample.

Figure 10A:
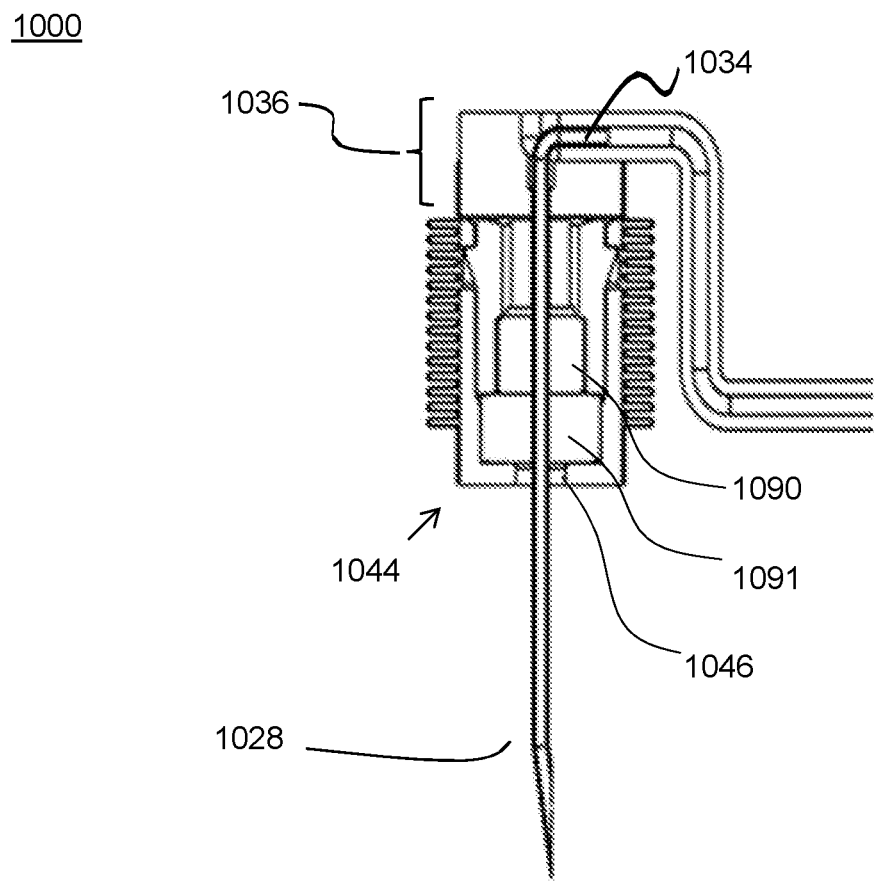
Figure 10B:
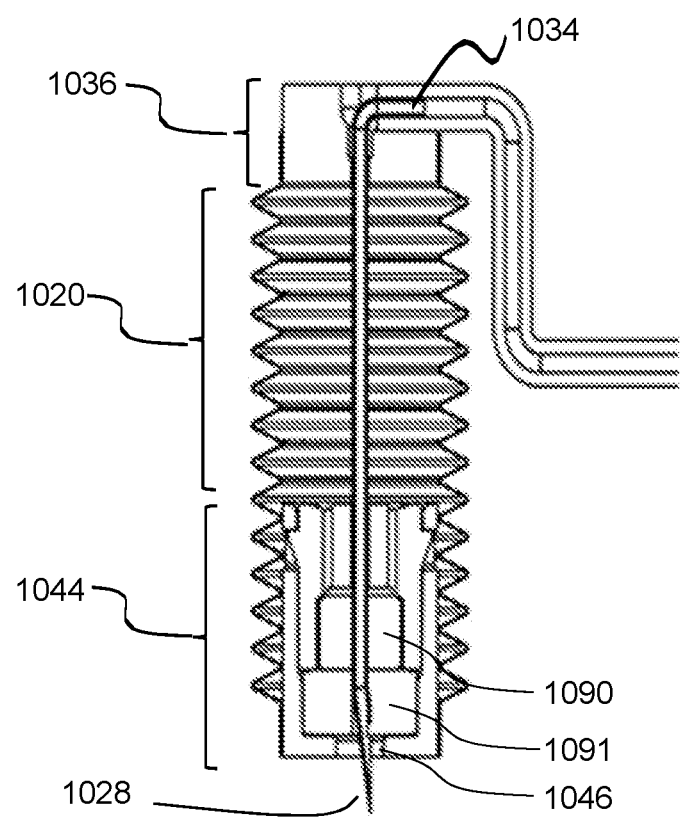

In still another related embodiment a dual septum configuration is provided, shown generally in FIGS. 10A-D, which can also be incorporated into any of the other embodiments herein. As with the other embodiments, the dual septum configuration preferably includes a chamber 1020, which itself includes a collapsible sidewall 1026 connected to an upper body 1036 and a lower body 1044. Again, the chamber 1020 is characterized in that it has a collapsed state (FIG. 10A) and an expanded state (FIGS. 10C-D). For completeness, FIG. 10B shows an intermediate step during expansion. In preferred embodiments, the lower body 1044 is sized and/or shaped for friction fitting into a mounting base akin to FIG. 1.

As shown in FIG. 10A, the collapsed state is further characterized as having a needle 1028, preferably a non-coring or Huber needle affixed to the upper body 1036, passing through the lower body 1044 and thus being capable of accessing a patient's implanted medical port. Fluid connection between a remote source, including but not limited to a syringe or infusion pump, and the needle 1028 is accomplished in part through a first channel 1034 within the upper body 1036, which itself is positioned at the upper end of the chamber 1020. In particular, the first channel 1034 of the upper body 1036 is fluidly connected to the needle 1028 and can be fluidly coupled to tubing 1038 thereby permitting infusion from a remote pumping source such as the syringe or infusion pump. Accordingly, a liquid medication can pass across through the first channel 1034, through the needle 1028 and into the patient.

In contrast, FIG. 10D depicts an expanded state (also referred to as a deployed state), characterized as having the bevel or tip of the needle 1028 at or above the bottom most plane of the lower body 1044 to prevent passage of fluid out of the lower body 1044. Transitioning from a collapsed state to an expanded state, depicted generally in FIG. 10C, can occur by pulling the upper body 1036 or by filling the chamber 1020 by pumping a fluid through a second channel (not shown but demonstrated throughout FIGS. 1-9) that openly terminates to empty into the chamber 1020. The chamber 1020 can be further guided upward through the addition of an external mechanical guide positioned outside of the collapsible sidewall 1026 that upwardly guides the upper body 1036 from the lower body 1044 during expansion thereby further reducing wobble of the upper body 1036 and thus needle 1028 during expansion of the chamber 1020. The external mechanical guide can be joined at the lower end to the lower body 1044 and at the upper end to the upper body 1036.

The dual septum configuration was found to further improve sealing over wider testing parameters, yet still permits the needle 1028 to be easily retracted. Preferably, the lower septum 1191 is attached to the lower body 1144, and the upper septum 1090 is pressed against or attached to the lower septum 1091. Attachment can be by way of adhesive, fusing or any other suitable means for attachment known by those skilled in the art to which the invention belongs. As shown in FIG. 10C, while the needle 1028 is being drawn upwards through the lower body 1044, the lower septum 1091 closes completely while the upper septum 1090 occludes the needle 1028. In some embodiments, the needle 1028 continues to move upwards and out of the upper septum 1090, as shown in FIG. 10D.

A septum's sealing pressure is characterized by (1) the force of compression on the needle 1028 when the needle 1028 is within a septum, (2) the tightness of the seal when the needle 1028 is not within the septum, and (3) the level of pressure that the seal is able to withstand before breaking or opening. By using the double septum approach, the sealing pressure of the lower septum 1091 can be increased to ensure a tight seal. Simultaneously, a lower relative sealing pressure in the upper septum 1090 ensures effective occlusion and ease of retraction. Increasing the sealing pressure of the septum may be by way of increasing compression of its material during formation. While a variety of polymers may be used to form the septums, each is preferably formed from silicone.

The dual septum configuration was surprisingly found to have certain benefits over a wider range of use than a single septum system. Experimentally it was found that in some instances when using a single septum as a pierceable barrier, the user did not completely withdraw the needle from the septum/barrier, and in some of these instances fluid entering the chamber through the second channel ingressed into the septum and hydraulically forced open the septum causing leakage.

Accordingly, the invention also provides a medical infusion device 1000, which includes a chamber 1020 characterized by an upper body 1036 joined to a lower body 1044 by a reversibly collapsible sidewall 1026, where the upper body 1036 has a first channel 1034 fluidly coupled to a needle 1028, and the lower body 1044 has a pierceable barrier characterized as a lower septum 1091 vertically aligned beneath an upper septum 1090 and where the lower septum 1091 forms a higher pressure seal than the upper septum 1090. The chamber 1020 has a collapsed state and an expanded state, where the collapsed state is characterized as the sidewall 1026 being collapsed and the needle 1028 piercing entirely through the lower septum 1091 to deliver a fluid outside of the device 100, and the expanded state characterized as the needle less than entirely piercing through the lower septum 1091.

In each dual septum configuration, the lower septum 1091 closes completely even while the upper septum 1090 remains partially open due to the presence of the retracted needle 1028 in the upper septum 1090. Using this technical approach, it was found that risk of hydraulic force opening the lower septum 1091, and thus the pierceable barrier 1046, was significantly reduced over a wide range of users. In other words, separating the septums into two allows the lower septum 1091 to fully close so that it cannot be pried open by the needle 1028 and hydraulic pressure. Thus, the dual septum configuration reduces the risk of contamination by its sequential sealing effect over a wider range of use.

Relatedly, having a lower septum 1091 and an upper septum 1090 sequentially stacked permits the lower septum 1091 to be configured with a much tighter seal to withstand higher pressures. A tighter seal reduces the risk of contamination and is thus a safer seal. A high pressure seal is able to withstand high pressures acting on it, without the seal opening. However, a septum with a tight, high pressure seal also compresses the needle 1028 and induces high frictional drag on the needle 1028 while the needle 1028 is being drawn upwards or lowered downwards. A high frictional drag on the needle 1028 could increase chance of user error. The dual septum configuration solves this challenge by providing an upper septum 1090 and a lower septum 1091 and pressing them together allows the lower septum 1091 to be configured with a high pressure seal, while keeping the upper septum 1090 as a lower pressure, preventive seal. Lowering seal pressure of the upper septum 1090 reduces the drag on the needle 1028 while the needle is being drawn upwards or lowered downwards. Lowering the sealing pressure in the upper septum 1090 offsets the drag from the lower septum 1091. Thus, the dual septum configure provides a completely closed high pressure seal, together with relatively low needle drag.

The dual septum configuration is compatible with any of the configurations shown in FIGS. 1-9. Furthermore, the upper body 1036 and lower body 1044 may be formed using conventional injection molding techniques with suitable polymers used in the formation of many medical devices such as polypropylenes or other polymers. Similarly, the sidewall 1026 of the chamber 1020 may be formed from rubber or foldable polymer then adhered or fused to the upper body 1036 and lower body 1044. The lower body 1044 may be provided with an aperture that is covered or filled with self-sealing polymer or silicone to form the pierceable barrier 1046, which itself may be part of the lower septum 1091.

Each septum, 1090, 1091, can be formed from materials and manufacturing methods known to those in the medical device field. Each septum can be formed from a variety of materials that reversibly seal. Preferably the each septum 1090, 1091 is formed from silicone but any self-sealing polymer known in the medical device arts would be suitable.

Accordingly, use of the device as shown in FIGS. 10A-D can provide a method of delivering medication into or through an implanted medical port, which includes providing the infusion device 1000 in a collapsed configuration, aligning the needle 1028 with an implanted infusion port, and pressing the infusion device such that needle 1028 pierces the patient's skin, then into the septum of the implanted port. To further assist with insertion or handling, the uppermost portion of the upper body 1036, or a portion of the lower body 1044 may be flattened, convex, concave, flanged, curved or suitably shaped to accept a hand or finger to assist in securely gripping or pressing the infusion device 1000. Once the needle 1028 pierces the skin and is inserted into the patient's infusion port, the lower body 1044 can be adhesively mounted to the patient through the use of adhesive mounts positioned along the underside of the lower body 1044 or by applying tape over outward extending flanges of the lower body 1044. Infusion of a medical sample is accomplished by delivering the sample through the first channel 1034, which is fluidly coupled to the needle 1028, and into the implanted infusion port.

After infusion is complete, the user can either pull on the upper body 1036 to retract the needle or introduce a fluid into the expandable chamber 1020 to upwardly extend the chamber sidewall 1026 to retract the needle 1028 (as in described in FIGS. 1-9). In such alternative approaches skilled artisan will appreciate that the fluid may be any suitable fluid such as water, saline, phosphate buffered saline, wash solution, bleach solution or other liquids. Alternatively, compressed gas, such as compressed air, can be applied to the chamber 1020.

In a preferred method, the needle 1028 is retracted completely from the lower septum 1091. In some embodiments the bevel or tip of the needle 1028 is retracted to terminate at the upper septum 1090 for occlusion. In some embodiments the bevel or tip of the needle 1028 is retracted entirely to terminate above the upper septum 1090.

In still further embodiments the method includes introducing fluid into the chamber to wash the needle (through a second channel consistent with FIGS. 1-9). In embodiments, which include the second channel, continued flow of solution into the chamber would then backflush the needle 1028, first channel 1034, and optional tubing. As with the embodiment above, a visual indicator may be employed to monitor backflushing to ensure removal of potentially hazardous medication or solution and therefore may notify the user when the device 1000 may be disposed of without special designation as a hazardous material. Further protection against needle stick can be accomplished by providing a blocking structure, as shown in FIGS. 7A-B, configured to block access through the pierceable barrier 1046 by the needle 1028 upon expansion.

Figure 11A:
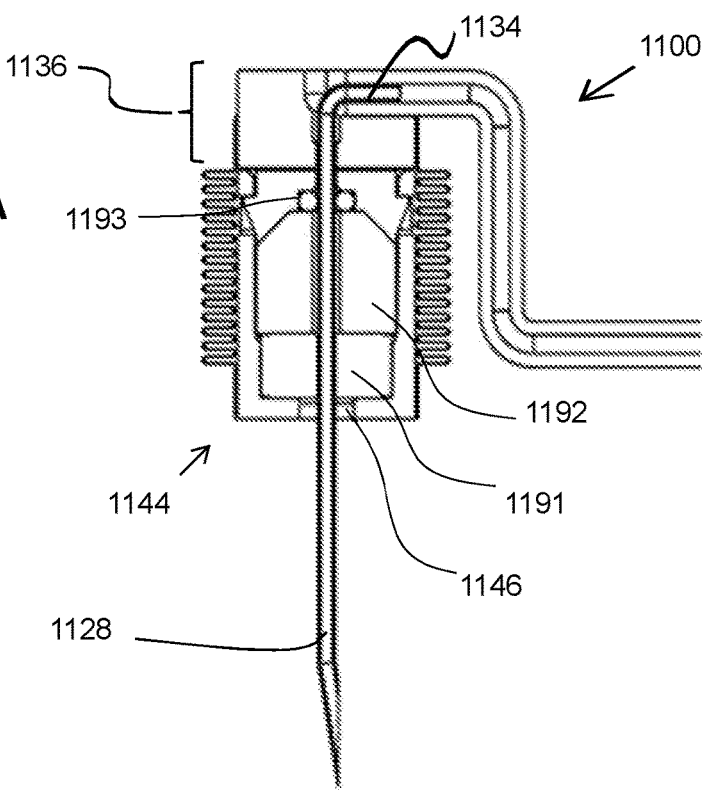
FIGS. 11A-C depict an infusion device configured with an additional o-ring seal.
Figure 11B:
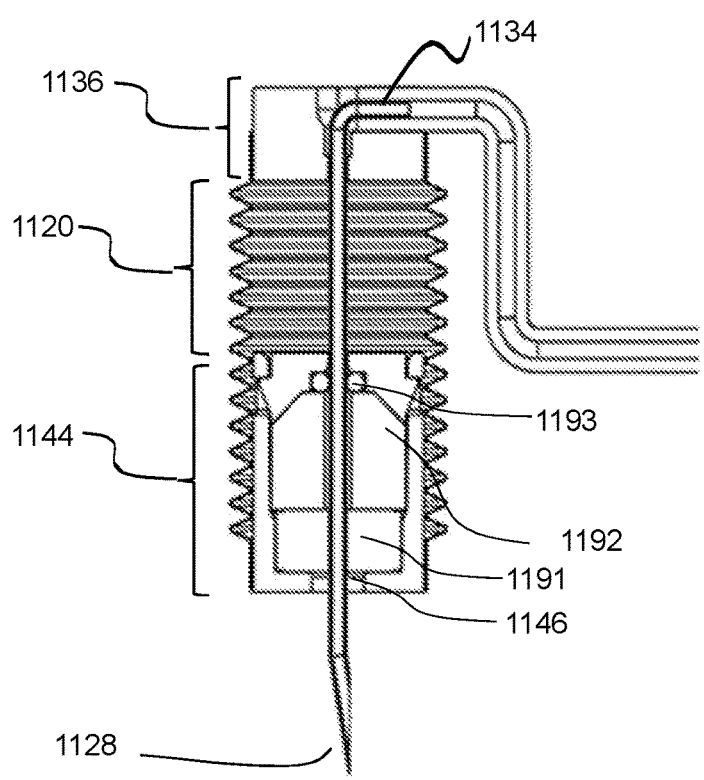
Figure 11C:
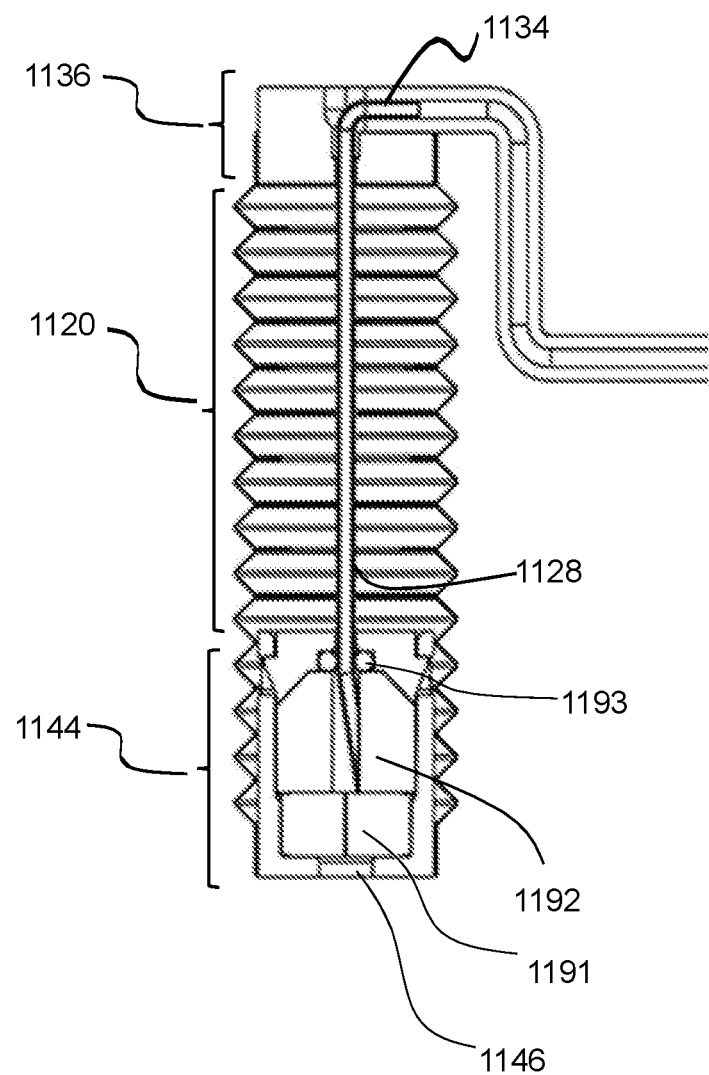

A variation of the previous embodiment shown in FIGS. 10A-D, is shown in FIGS. 11A-C. The embodiment shown in FIGS. 11A-C is substantially the same as that shown in FIGS. 10A-D, except the upper septum 1090 is replaced by a channeled housing 1192, preferably a rigid cylindrical housing 1192, and an o-ring 1193 is stacked sequentially above the cylindrical housing 1192 for sealing the channel.

Accordingly, a medical infusion device 1100, is provided, which includes a chamber 1120, an upper body 1136, a lower body 1144, and a collapsible sidewall 1126. The upper body 1136 is located above the chamber 1120, and the lower body 1144 is located below the chamber 1120. The chamber 1120 has a collapsible sidewall 1126. The chamber 1120 is characterized in that it has a collapsed state (FIG. 11A), an expanded state (FIG. 11C), and an intermediate state during expansion (FIG. 11B). The skilled artisan would appreciate that the lower body 1144 could be divided into a detachable mounting base with lower body insert more akin to FIG. 1 if desired. As shown in FIG. 11A, the collapsed state is further characterized as having a needle 1128, preferably a non-coring or Huber needle affixed to the upper body 1136, passing through the lower body 1144 and thus being capable of accessing a patient's implanted medical port. Fluid connection between a remote source, including but not limited to a syringe or infusion pump, and the needle 1128 is accomplished in part through a first channel 1134 within an upper body 1136, which itself is positioned at the upper end of the chamber 1120. In particular, the first channel 1134 of the upper body 1136 is fluidly connected to the needle 1128 and can be fluidly coupled to tubing thereby permitting infusion from a remote pumping source such as the syringe or infusion pump. Accordingly, a liquid medication can pass across through the first channel 1134, through the needle 1128 and into the patient.

In contrast, FIG. 11C depicts an expanded state (also referred to as a deployed state), characterized as having the bevel or tip of the needle 1128 at or above the bottom most plane of the lower body 1144. Transition from a collapsed state to an expanded or deployed state can occur by pulling the upper body 1136 or by filling the chamber 1120 with a fluid through a second channel (consistent with an approach in FIGS. 1-9) within the upper body 1136. The chamber 1120 can be further guided upward through the addition of an external mechanical guide positioned outside of the collapsible sidewall 1126 that upwardly guides the upper body 1136 from the lower body 1144 during expansion thereby further reducing wobble of the upper body 1136 and thus needle 1128 during expansion of the chamber 1120. The external mechanical guide can be joined at the lower end to the lower body 1144 and at the upper end to the upper body 1136.

In the embodiment shown in FIGS. 11A-C, the lower body 1144 has a septum 1191 and a housing 1192 enclosing the needle 1128, and an o-ring 1193. The housing 1192 is preferably cylindrical. The lower end of the housing 1192 is sealably attached to the septum 1191, while the upper end of the housing 1192 is attached to the o-ring 1193 such that in combination with the needle 1128, the o-ring 1193 and the housing 1192 create a seal around the needle 1128, isolating the septum 1191 and the pierceable barrier 1146 from pressure within the lower body 1144 and/or within the chamber 1120. The attachment can be provided by any means known in the art by the skilled artisan, such as an appropriate adhesive.

Figure 12A:
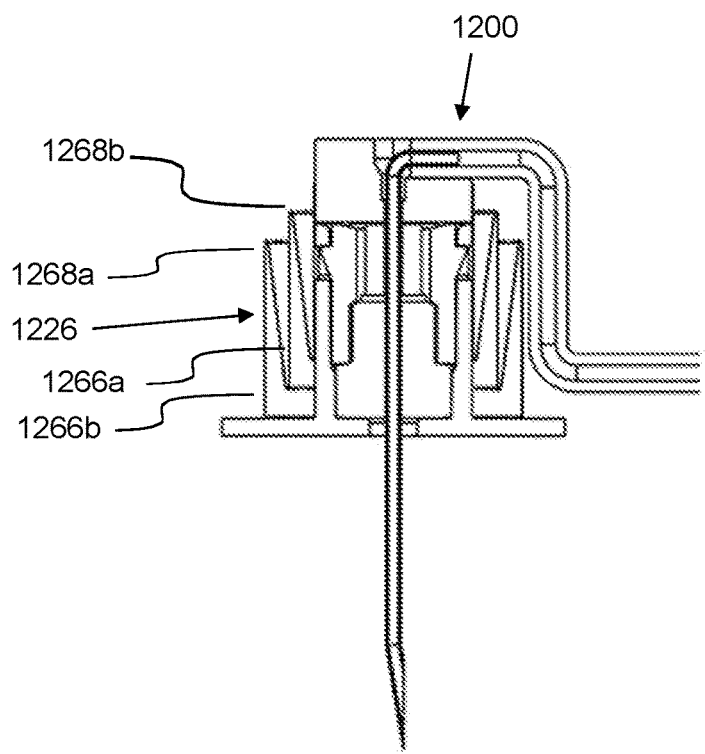
FIGS. 12A-B depicts an alternative bellows configuration with concentric nesting of the sidewall.
Figure 12B:
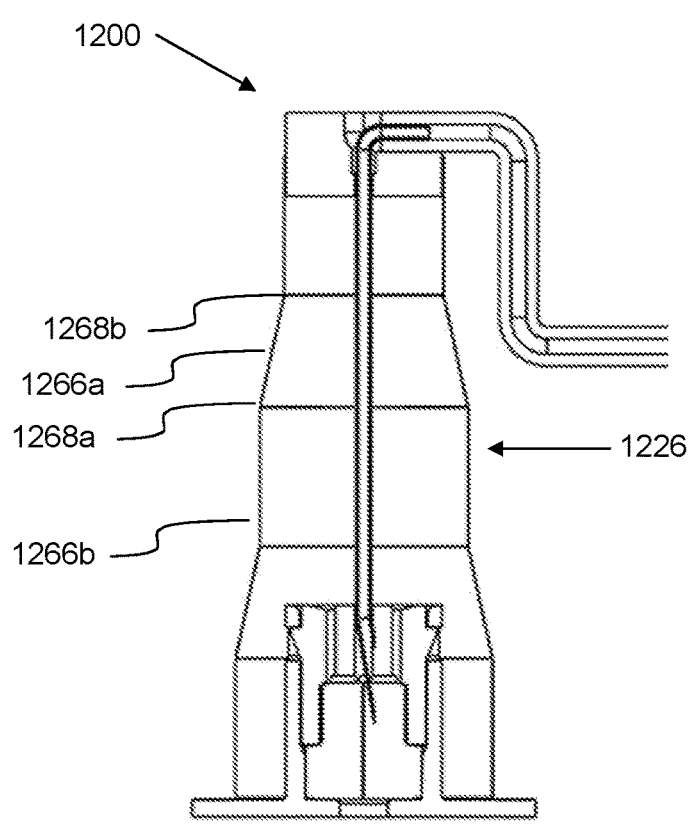

FIGS. 12A-B show an alternative configuration of the collapsible sidewall 1226. The collapsible sidewall 1226 in FIGS. 12A-B can be used in the previous embodiments interchangeably with the sidewalls shown therein.

The collapsible sidewall 1226 is provided as a series of segments 1266a, 1266b, between alternating folds 1268a, 1268b, that are foldable in a concentrically nested manner. Being foldable in a concentrically nested manner is characterized in that, while in the collapsed state (FIG. 12A), the segments 1266 are collapsed into a substantially vertical alignment with one another. The segments 1266a and 1266b are further optionally characterized in that while in an expanded state (FIG. 12B), the segments 1266 are in a substantially vertical alignment with one another. The segments 1266a, 1266b between folds 1268a, 1268b, can be rigid, flexible, bendable, semi-flexible, and/or stretchable. The concentrically nested sidewall 1226, when in the collapsed configuration (FIG. 12A), provides for a lower overall height of the device 1200, which, among other advantages, allows for a lower, more economical packaging volume when shipping the device 1200.

The invention described herein may be embodied in other specific forms without departing from the spirit or essential characteristics thereof. The specific embodiments previously described are therefor to be considered as illustrative of, and not limiting, the scope of the invention.

What is claimed is:

1. A medical infusion device comprising:
   a chamber characterized by an upper body joined to a lower body by a reversibly collapsible sidewall, wherein the upper body comprises a first channel fluidly coupled to a needle and a second channel fluidly coupled to an interior of the chamber at a position distinct and separate from the first channel, the lower body comprising a pierceable barrier that can be pierced by the needle;
   wherein the chamber has a collapsed state and an expanded state, the collapsed state characterized as the sidewall being collapsed, the needle piercing entirely through the pierceable barrier to deliver a liquid outside of the device, and the second channel fluidly connected to an interior of the chamber, the expanded state characterized as the needle less than entirely piercing through the pierceable barrier and the chamber capable of retaining a liquid, wherein the chamber is configured to hydraulically transition from the collapsed state to the expanded state by introducing liquid into the interior of the chamber through the second channel to volumetrically expand the chamber.

2. The medical infusion device according to claim 1, wherein the needle is a non-coring needle and the pierceable barrier is a self-sealing septum.

3. The medical infusion device according to claim 1, wherein the sidewall comprises a bellows configuration formed as a plurality of segments joined by alternating folds configured to fold and unfold at predetermined fold lines.

4. The medical infusion device according to claim 1, wherein the sidewall comprises segments that concentrically nest in the collapsed state.

5. The medical infusion device according to claim 1, wherein the first channel and the second channel do not intersect in the upper body.

6. The medical infusion device according to claim 1, wherein the second channel terminates at the interior of the chamber in both the collapsed state and the expanded state.

7. The medical infusion device according to claim 1, wherein the pierceable barrier is configured as a lower septum positioned below an upper septum.

8. The medical infusion device according to claim 7, wherein the lower septum forms a higher pressure seal compared to the upper septum.

9. The medical infusion device according to claim 1, wherein the upper body further comprises a hydrophobic filter configured to permit outgassing of the chamber.

10. The medical infusion device according to claim 1, further comprising a valve that selectively directs flow of liquid from outside of the device into the first channel or the second channel.

11. The medical infusion device according to claim 10, wherein the valve forms part of the upper body.

12. The medical infusion device according to claim 1, further comprising a blocking structure positioned within the chamber and configured to block access to the pierceable barrier by the needle when the chamber is in the expanded state.

13. The medical infusion device according to claim 1, further comprising a rigid sheath that sheathes the needle in the expanded state.

14. A method of delivering medication into an implanted medical port, the method comprising:
   providing the medical infusion device according to claim 1 in the collapsed state;
   piercing the implanted medical port with the needle;
   infusing medication into the medical port through the needle via the first channel;
   introducing liquid into the chamber via the second channel thereby volumetrically expanding the chamber to withdraw the needle from the medical port.

15. The method according to claim 14, wherein the pierceable barrier is configured as a lower septum positioned below an upper septum, the method further comprising retracting the needle completely from the lower septum.

16. The method according to claim 15, wherein the bevel or tip of the needle is retracted into the upper septum.

17. The method according to claim 16, wherein the bevel or tip of the needle is retracted entirely through the upper septum.

18. The method according to claim 17, further comprising continuing to introduce liquid into the chamber to wash the needle.

19. The method according to claim 18, wherein the first channel is fluidly coupled to exterior tubing, the method further comprising continuing to introduce liquid into the chamber to backflush the first channel and exterior tubing.

* * * * *